US009682247B2

(12) United States Patent
Susedik et al.

(10) Patent No.: US 9,682,247 B2
(45) Date of Patent: Jun. 20, 2017

(54) APPARATUS FOR THE GENERATION OF AN ENERGY FIELD FOR THE TREATMENT OF CANCER IN BODY CAVITIES AND PARTS THAT ARE CAVITY-LIKE

(71) Applicant: Endomagnetics Limited, Cambridge (GB)

(72) Inventors: Michael Edward Susedik, Boulder, CO (US); Karl Michael Frantz, Broomfield, CO (US); Daniel Bernard McKenna, Vail, CO (US); Martin Albert Huisjen, Boulder, CO (US); Carolyn Perry Adams, Boulder, CO (US)

(73) Assignee: ENDOMAGNETICS LIMITED, Cmbridge (GB)

( * ) Notice: Subject to any disclaimer, the term of this patent is extended or adjusted under 35 U.S.C. 154(b) by 0 days.

(21) Appl. No.: 14/797,526

(22) Filed: Jul. 13, 2015

(65) Prior Publication Data
US 2015/0367140 A1  Dec. 24, 2015

Related U.S. Application Data

(63) Continuation of application No. 13/590,737, filed on Aug. 21, 2012, now abandoned.
(Continued)

(51) Int. Cl.
*A61M 37/00* (2006.01)
*A61N 2/00* (2006.01)
(Continued)

(52) U.S. Cl.
CPC ............. *A61N 2/002* (2013.01); *A61M 25/10* (2013.01); *A61M 37/00* (2013.01); *A61N 1/406* (2013.01);
(Continued)

(58) Field of Classification Search
CPC .......... A61K 2035/124; A61K 41/0052; A61K 49/1863; A61K 49/1896; B82Y 5/00; C12N 5/0663; C12N 2529/00; A61N 5/10
(Continued)

(56) References Cited

U.S. PATENT DOCUMENTS

| 4,346,715 A | 8/1982 | Gammell |
| 5,099,756 A | 3/1992 | Franconi et al. |

(Continued)

FOREIGN PATENT DOCUMENTS

| CN | 1694657 | 11/2005 |
| CN | 101854977 | 10/2010 |

(Continued)

OTHER PUBLICATIONS

Machine Translation in English of JP07213507, Aug. 15, 1995 (attached).*
(Continued)

*Primary Examiner* — Navin Natnithithadha
*Assistant Examiner* — Sunita Reddy
(74) *Attorney, Agent, or Firm* — K&L Gates LLP

(57) ABSTRACT

The body cavity cancer treatment apparatus generates the magnetic field for use in a combined "low temperature hyperthermia" and ionizing radiation and/or chemotherapy cancer treatment protocol. Unlike other competing systems, the body cavity cancer treatment apparatus does not directly kill or ablate the cancer cells with killing temperatures rather, the body cavity cancer treatment apparatus stresses the cancer and cancer stem cells by keeping them at a nominal 42° C. for some period of time via the heating of nano-particles that have been infused into the bladder, using the generated magnetic field.

20 Claims, 19 Drawing Sheets

Related U.S. Application Data

(60) Provisional application No. 61/527,928, filed on Aug. 26, 2011, provisional application No. 61/527,973, filed on Aug. 26, 2011.

(51) Int. Cl.
    *A61N 1/40* (2006.01)
    *A61M 25/10* (2013.01)
    *A61N 2/02* (2006.01)
    *A61N 5/10* (2006.01)

(52) U.S. Cl.
    CPC .............. *A61N 2/004* (2013.01); *A61N 2/02* (2013.01); *A61M 2025/105* (2013.01); *A61M 2037/0007* (2013.01); *A61M 2205/3368* (2013.01); *A61N 5/10* (2013.01)

(58) Field of Classification Search
    USPC .......... 600/2, 9, 10, 12, 13; 24/9.3; 977/773, 977/706; 128/897–899
    See application file for complete search history.

(56) References Cited

U.S. PATENT DOCUMENTS

| | | | |
|---|---|---|---|
| 5,621,188 A * | 4/1997 | Lee | A61N 1/14 174/390 |
| 6,149,576 A | 11/2000 | Gray et al. | |
| 6,165,440 A | 12/2000 | Esenaliev | |
| 6,238,421 B1 | 5/2001 | Günther et al. | |
| 6,423,056 B1 * | 7/2002 | Ishikawa | A61B 5/0008 600/12 |
| 6,530,944 B2 | 3/2003 | West et al. | |
| 6,733,434 B2 | 5/2004 | Jacobson | |
| 6,819,210 B2 | 11/2004 | Boynton et al. | |
| 6,961,620 B2 | 11/2005 | Rioux et al. | |
| 6,997,863 B2 | 2/2006 | Handy et al. | |
| 7,133,725 B2 | 11/2006 | Stirbl et al. | |
| 7,174,217 B2 | 2/2007 | Rioux et al. | |
| 7,301,633 B2 | 11/2007 | Gibbs et al. | |
| 7,623,908 B2 | 11/2009 | Boppart et al. | |
| 7,819,835 B2 | 10/2010 | Landy et al. | |
| 7,842,281 B2 | 11/2010 | Haik et al. | |
| 7,951,061 B2 | 5/2011 | Foreman et al. | |
| 8,052,591 B2 | 11/2011 | Mishelevich et al. | |
| 2001/0012912 A1 | 8/2001 | Feucht | |
| 2002/0091377 A1 | 7/2002 | Anderson et al. | |
| 2002/0193784 A1 | 12/2002 | McHale et al. | |
| 2003/0032995 A1 | 2/2003 | Handy et al. | |
| 2004/0236278 A1 | 11/2004 | Herweck et al. | |
| 2005/0015049 A1 | 1/2005 | Rioux et al. | |
| 2005/0059852 A1 | 3/2005 | Rioux et al. | |
| 2005/0090732 A1 | 4/2005 | Ivkov et al. | |
| 2005/0171433 A1 | 8/2005 | Boppart et al. | |
| 2005/0215988 A1 | 9/2005 | Altshuler et al. | |
| 2005/0249817 A1 | 11/2005 | Haik et al. | |
| 2005/0271745 A1 * | 12/2005 | Gruettner | A61K 33/26 424/646 |
| 2006/0015098 A1 | 1/2006 | Rioux et al. | |
| 2006/0142748 A1 | 6/2006 | Foreman et al. | |
| 2006/0269612 A1 | 11/2006 | Xiang et al. | |
| 2007/0010702 A1 | 1/2007 | Wang et al. | |
| 2007/0135373 A1 | 6/2007 | Li et al. | |
| 2007/0258889 A1 | 11/2007 | Douglas et al. | |
| 2008/0103355 A1 | 5/2008 | Boyden et al. | |
| 2008/0114429 A1 | 5/2008 | Nagano et al. | |
| 2008/0300571 A1 | 12/2008 | LePivert | |
| 2008/0319375 A1 | 12/2008 | Hardy | |
| 2009/0043256 A1 | 2/2009 | Landy et al. | |
| 2009/0054722 A1 | 2/2009 | Sugano et al. | |
| 2009/0076496 A1 | 3/2009 | Azure | |
| 2009/0076502 A1 | 3/2009 | Azure et al. | |
| 2009/0157069 A1 | 6/2009 | Tom et al. | |
| 2009/0220968 A1 | 9/2009 | Issadore et al. | |
| 2009/0287036 A1 | 11/2009 | Shapiro et al. | |
| 2010/0016783 A1 | 1/2010 | Bourke, Jr. et al. | |
| 2010/0052668 A1 * | 3/2010 | Gleich | A61B 5/05 324/239 |
| 2010/0056643 A1 | 3/2010 | Bachynsky et al. | |
| 2010/0099941 A1 | 4/2010 | Haik et al. | |
| 2010/0160483 A1 | 6/2010 | Vogt et al. | |
| 2010/0185042 A1 | 7/2010 | Schneider et al. | |
| 2010/0204674 A1 | 8/2010 | Forbes et al. | |
| 2010/0222774 A1 | 9/2010 | Hegg et al. | |
| 2010/0256439 A1 | 10/2010 | Schneider et al. | |
| 2010/0292564 A1 | 11/2010 | Cantillon Murphy | |
| 2010/0310636 A1 | 12/2010 | Sharma et al. | |
| 2011/0104305 A1 | 5/2011 | Day et al. | |
| 2011/0125232 A1 | 5/2011 | Landy et al. | |
| 2011/0137230 A1 | 6/2011 | Altshuler et al. | |
| 2011/0177153 A1 | 7/2011 | Zhu | |
| 2011/0301401 A1 | 12/2011 | Larson et al. | |
| 2012/0065492 A1 * | 3/2012 | Gertner | A61B 5/055 600/411 |
| 2012/0203050 A1 | 8/2012 | Levy et al. | |
| 2012/0259154 A1 | 10/2012 | Hong et al. | |
| 2012/0302821 A1 | 11/2012 | Burnett | |
| 2013/0053619 A1 | 2/2013 | McKenna et al. | |
| 2013/0053620 A1 | 2/2013 | Susedik et al. | |
| 2013/0211249 A1 | 8/2013 | Barnett et al. | |

FOREIGN PATENT DOCUMENTS

| | | |
|---|---|---|
| CN | 102008782 | 4/2011 |
| JP | 04-276263 A | 10/1992 |
| JP | 04-348765 A | 12/1992 |
| JP | 05-245217 A | 9/1993 |
| JP | 07-213507 A | 8/1995 |
| JP | 2005-523736 A | 8/2005 |
| JP | 2007500060 A | 1/2007 |
| JP | 2007521109 A | 8/2007 |
| JP | 2010-512910 A | 4/2010 |
| JP | 2011-032238 A | 2/2011 |
| WO | 03/022360 A3 | 3/2003 |
| WO | 2004033038 A2 | 4/2004 |
| WO | 2004105833 A2 | 12/2004 |
| WO | 2005044365 A2 | 5/2005 |
| WO | 2010139386 | 12/2010 |

OTHER PUBLICATIONS

Machine Translation in English of JP04348765, Aug. 15, 1995 (attached).*
Barnes et al., Bioengineering and Biophysical Aspects of Electromagnetic Fields, Third Edition, 2007, pp. 298-299.
Vertegel et al., "Silica Nanoparticle Size Influences the Structure and Enzymatic Acitvity of Absorbed Lysozyme," Langmuir, 2004, vol. 20, pp. 6800-6807.
International Search Report in corresponding PCT Application No. PCT/US2012/051763 dated Oct. 22, 2012, 3 pages.
International Search Report in corresponding PCT Application No. PCT/US2012/051765 dated Oct. 22, 2012, 3 pages.
International Search Report in corresponding PCT Application No. PCT/US2011/068114 dated Apr. 19, 2012, 3 pages.
International Search Report in corresponding PCT Application No. PCT/US2011/068116 dated May 8, 2012, 3 pages.
International Search Report in corresponding PCT Application No. PCT/US2011/068134 dated May 8, 2012, 3 pages.
International Search Report in corresponding PCT Application No. PCT/US2011/068142 dated May 4, 2012, 3 pages.
International Search Report in corresponding PCT Application No. PCT/US2011/068146 dated May 2, 2012, 3 pages.
International Search Report in corresponding PCT Application No. PCT/US2011/068154 dated May 3, 2012, 3 pages.
Wikipedia Physics of magnetic resonance imaging (2014), retrieved on Aug. 5, 2014 from http://en.wikipedia.org/wiki/Physics_of_magnetic_resonance_imaging, 13 pages.
Giustini, et al. "Magnetic Nanoparticle Hyperthermia in Cancer Treatment" Nano Life, Mar. 2010.

(56) References Cited

OTHER PUBLICATIONS

In the U.S. Patent and Trademark Office U.S. Appl. No. 13/012,572 Non-Final Office Action dated May 23, 2013, 12 pages.
In the U.S. Patent and Trademark Office U.S. Appl. No. 13/012,560 Non-Final Office Action dated Apr. 25, 2013, 9 pages.
In the U.S. Patent and Trademark Office U.S. Appl. No. 13/012,527 Non-Final Office Action dated Apr. 29, 2013, 13 pages.
Sophie Laurenta et al. "Magnetic Fluid Hyperthermia: Focus on superparamagnetic iron oxide nanoparticles" Advances in Colloid and Interface Science, vol. 155, Issues 1-2, Aug. 10, 2011.

* cited by examiner

APPARATUS FOR THE GENERATION OF AN ENERGY FIELD FOR THE TREATMENT OF CANCER IN BODY CAVITIES AND PARTS THAT ARE CAVITY-LIKE

CROSS-REFERENCE TO RELATED APPLICATIONS

This application is a continuation patent application claiming priority to U.S. patent application Ser. No. 13/590,737 filed Aug. 21, 2012, which claims priority to U.S. provisional application No. 61/527,928 filed on Aug. 26, 2011 and U.S. provisional application No. 61/527,973 filed on Aug. 26, 2011, the entire disclosures of each of which are herein incorporated by reference.

FIELD OF THE INVENTION

The invention relates generally to the field of treatment of invasive agents, such as pathogens and cancers, in living organisms such as the human body and, more particularly, to a system that generates an energy field for application to the living organism, to activate nano-particles which are infused into the living organism.

BACKGROUND OF THE INVENTION

Any time low temperature heat is added to a living organism, such as the human body, as it is being treated for cancer with radiation and/or chemotherapy, the efficacy of the cancer treatment is substantially increased. The difficulty with this process has been in "adding heat" to only the cancerous region that is being treated, in a precisely controlled manner.

One prior cancer treatment method sought to place the entire living organism in a hot water wrap which often caused severe side effects, including death, since the control of the patient's body temperature is not precise. This cancer treatment method often caused conditions similar to heat shock or heat stroke, since the living organism is unable to adequately remove the applied heat to maintain a safe body temperature.

Another cancer treatment approach, called regional hyperthermia, uses microwave energy, applied to the living organism from an external source, to heat the tissue. This approach relies on the fact that tissue is largely composed of water, which is dipolar in nature and heats as the water molecules "physically flip" in concert with the applied alternating current magnetic field. This "flip" causes molecular friction, hence heat. However, the microwave heating of tissue causes hot spots and burns (as do microwave ovens). In addition, it is virtually impossible to direct the microwave energy to only heat the tissue of interest and surrounding non-cancerous tissue is therefore also heated, sometimes to a burning level. Studies have shown patients can receive $2^{nd}$ degree and $3^{rd}$ degree burns from a microwave heating approach.

A third cancer treatment approach uses an "antenna," such as a monopole, which is inserted via a catheter inside the body cavity to be heated. As before, severe hot spots and burns can result from the non-uniform application of electromagnetic fields (at microwave frequencies) which has unintended damaging effects.

All of the cancer treatment methods embodied in the present prior art have significant deficiencies in terms of patient safety, treatment efficacy and cost. In addition, in the United States, the only approved procedure for the treatment of bladder cancer in humans is a pure chemotherapy-based approach, without any heating of the bladder tissue or the chemotherapy medicine, to stress and help kill remaining cancer cells. Other approaches, such as using microwave heating applied to the body from a source located outside the body, are only in experimental, pre-clinical studies. The catheter-based approach is only approved for use in certain European countries.

Thus, the present set of bladder cancer treatment methods can be characterized as:

Chemotherapy without hyperthermia—minimal effectiveness.

Radiation without hyperthermia—minimal effectiveness.

Chemotherapy with microwave heating of bladder tissue causes burns, non-uniform heating, hot spots, cold spots, patient pain, patient discomfort, and inadvertently heats non-bladder tissue.

Chemotherapy with catheter-based radio frequency heating inside the bladder space via a small antenna causes burns, non-uniform heating, hot spots, cold spots, patient pain and patient discomfort.

Circulating chemotherapy fluids without a catheter-based system won't work because of the physical size of the urethra, non-uniform thermodynamics (one cannot only remove "cold" fluid and replace it with "warm" fluid), re-circulating chemotherapy agents thru the urethra is caustic and very damaging, the urethra can be easily damaged by large physical objects inserted into it and lastly, the chemotherapy agent (such as Mitomycin C) is very expensive. All of this increases the volume of Mitomycin C required to ensure that the chemotherapy agent concentration is uniform in the total circulated volume of fluid (upwards of 4 to 5 times the nominal amount of Mitomycin C is necessary if circulated fluids are used).

BRIEF SUMMARY OF THE INVENTION

The present Apparatus for the Generation Of An Energy Field For The Treatment of Cancer in Body Cavities and Parts That Are Cavity-Like (termed "body cavity cancer treatment apparatus" herein) eliminates the weaknesses and deficiencies of existing cancer treatment systems by implementing a process that creates a "low temperature hyperthermia" condition in the body cavity in conjunction with ionizing radiation and/or chemotherapy. This combination of treatment protocols has the potential for improving the effectiveness of cancer treatments by at least 2-4 times in the long term, while lowering the level of required radiation or chemotherapy medicine. While the body cavity cancer treatment apparatus could be used to heat cancer cells to a killing temperature (46° Celsius and higher), it is believed that heating the cancer cells to a 5° C.-6° C. temperature increase over the body's ambient temperature (low temperature hyperthermia) realizes significant benefits without incurring the risks of heating to the higher cell-killing temperatures. Unlike other cancer treatment systems, the body cavity cancer treatment apparatus docs not directly kill or ablate the cancer cells with killing temperatures; rather, the body cavity cancer treatment apparatus stresses the cancer and cancer stem cells using hyperthermia by keeping them at a nominal 42° C.-43° C. temperature for some period of time, for example 30 to 60 minutes, temperature and protocol dependent as set by the treating physician.

The body cavity cancer treatment apparatus provides a systems-level approach to cancer treatment that achieves extremely uniform temperatures inside the tissue surrounding the body cavity, thereby realizing optimal efficacy while avoiding harm or pain to the patient. This is accomplished by the inclusion of "target particles," such as nano-particles, into the body cavity along with the chemotherapy agent to enable the body cavity cancer treatment apparatus to externally generate an energy field to cause heating of the chemotherapy agent and the surrounding tissue of the body cavity by activation of the nano-particles. The proper selection of the characteristics of the applied energy field enables precise control of the heat generated by the movement of the nano-particles. The body cavity cancer treatment apparatus uses exactly matched or paired nano-particles having a given material composition and set of material properties in concert with a precisely defined electromagnetic field, in this case a predominantly magnetic field. By using a magnetic field of certain properties and specifications, only the nano-particles heat while healthy tissue surrounding the region of cancer cells which contain the nano-particles does not heat.

An alternative to the procedure described above is the infusion of the chemotherapy agent into the bladder and the insertion of a "balloon" into the bladder. The balloon molds to the exact shape of the bladder, so nano-particles in a solution are put into the balloon, inflating the balloon and forcing the chemotherapy agent into the space between the balloon and the walls of the bladder. The solution of nano-particles in the balloon is heated via the application of an illumination energy field. The generated heat is transferred to both the bladder wall and the chemotherapy agent. At the end of the remaining portion of the procedure as noted above, the nano-particles are removed from the balloon and then the balloon is removed from the inside of the bladder, as is the chemotherapy agent. Alternatively, a fluid solution can be circulated through the balloon, without the use of the nano-particles, to maintain the temperature of the chemotherapy agent in the bladder.

In addition, the associated nano-particle delivery process is non-invasive, meaning the nano-particles are contained in a fluid which is inserted into the body cavity and then removed after the procedure. For certain types of cancer, this has many attendant advantages: (A) the nano-particles do not enter the bloodstream; (B) control of the exact concentration of nano-particles in a composite fluid usually containing a chemotherapy substance in solution (unless the protocol is pure ionizing radiation); (C) the known concentration of nano-particles enables much more precise heating illumination protocol; (D) the nano-particles are removed after the procedure and do not stay in the body; (E) pre-mixing of a chemotherapy agent with the nano-particle solution is easily achieved.

While the preferred embodiment disclosed herein is the use of the body cavity cancer treatment apparatus to implement a treatment protocol for bladder cancer, the apparatus described herein can be used for other "cavity-like" organs or body structures. Body organs such as the colon, uterus, vagina, cervix, esophagus, stomach, and so on, that are naturally a cavity or that can be blocked off to form a temporary cavity, are viable body parts for this safe and efficacious treatment protocol. Catheter-based balloons can be placed on either end of a cancerous region in a tubular-like structure to only treat that segment of the "tube." Alternative body regions for treatment are also surgery-developed cavities that leave a tissue void, for example removal of a tumor in the brain, where the procedure fills the void with nano-particles and a chemotherapy agent, then heats the tissue and chemotherapy agent via the application of an externally-generated magnetic field. Other surgical procedures that create a void, such as the removal of a tumor in the breast, could be treated using this approach.

There are a number of advantages that accrue using the treatment methods and protocols described herein:

Closed system for particle containment.

Particles are never introduced systemically.

Significant increase in the efficacy of the treatment.

Efficacy increases are upwards of 2-4 times; possibly significantly higher in certain cases.

This treatment re-uses existing chemotherapy and/or radiation treatment protocols and drugs in a new and novel method.

This treatment dramatically reduces the likelihood of burns, hot spots, cold spots, or inadvertent tissue heating.

DETAILED DESCRIPTION OF THE INVENTION

Low Temperature Hyperthermia

Figure 1A:
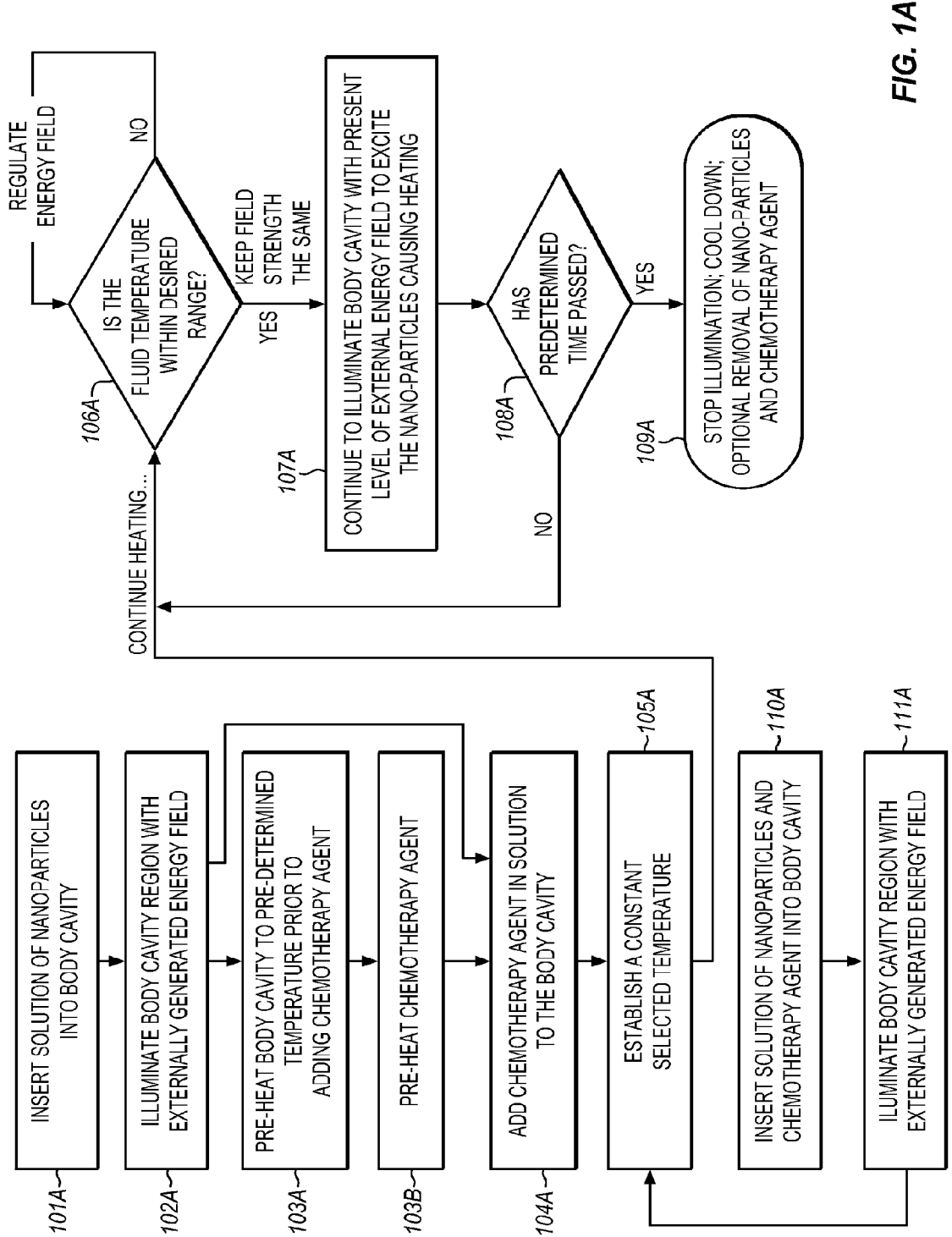
FIGS. 1A and 1B illustrate in flow diagram form the various steps of the protocol used to implement body cavity cancer treatment apparatus, and a bladder cancer treatment implementation of this process, respectively.

The combination of low temperature hyperthermia with ionizing radiation and/or chemotherapy has the potential for increasing the effectiveness of cancer treatments by 2-4 times, as noted above, while lowering the level of required radiation or chemotherapy medicine. One additional benefit of low temperature hyperthermia is re-oxygenation, where the level of oxygen in the tumorous regions is greatly increased. This is highly stressful to cancer and cancer stem cells in particular, which most decidedly prefer a hypoxic environment. Other significant biological benefits accrue when cancer is kept at a low temperature hyperthermia state, including acute acidification and reduction of Heat Shock Protein release (HSP). Other benefits accrue since ionizing radiation and low temperature hyperthermia each affect different phases of the cellular reproductive process, M and S.

From the body ambient temperature of 37° C. to a target temperature of between 42° C. and 43° C., every degree increase above 37° C. increases the effectiveness of chemotherapy medicines. Such enhancement of chemotherapy agent effectiveness can change the treatment outcome from a 10 year complete cure rate of, for example, 15%-20% without nano-particle based hyperthermia, typically to upwards of 50%-60% with nano-particle based hyperthermia for certain cancers, such as bladder cancer. This improvement in bladder cancer complete cure results is dramatic; it is expected as this technique is applied to other cancers and even other diseases that the similar efficacy and cure rates is evident.

Medicines, such as PARP inhibitors, interfere with the ability of cancer cells to self-repair damaged DNA in a given cancer cell. Thus, if the DNA in a given cancer cell is intentionally damaged and the PARP inhibitor prevents the cancer cell from "self-fixing" the DNA, the cancer cell will die. However, PARP inhibitors are not very effective unless the ambient temperature is elevated to the 42° C.-43° C. range. Note that hyperthermia is also very effective at interfering with cellular DNA reproduction. Thus, being able to increase the ambient temperature of the cancerous region from 37° C. to 42° C.-43° C. is essential for PARP inhibitors to be effective in stopping cancer cells from self-repairing their intentionally damaged DNA. Both the PARP inhibitor and the low temperature hyperthermia protocol, individually and in concert, impact/prevent the cancer cell's ability to repair the damaged cancer cell DNA. At the moment, it is believed that concurrent heating of the cancerous region is likely the most beneficial protocol but there may be reasons why a pre- or post-heating protocol relative to the timing of radiation or chemotherapy is preferred.

The nano-particles are activated by the body cavity cancer treatment apparatus which generates a precisely crafted energy field to provide illumination of the nano-particles with the minimum energy that is required to create the selected effects. The energy field characteristics are selected from the characteristics of energy fields including: field type; frequency; field strength; duration; field modulation; repetition frequency; beam size; and focal point, that are required to energize the nano-particles in a selected manner in the portion of the target living organism that is being treated. In addition, the mapping of characteristics of the energy field provides great flexibility and enables the concurrent use of multiple types of nano-particles.

It is important to note that the activation of nano-particles by the body cavity cancer treatment apparatus is highly deterministic, meaning that a given particle is optimally activated or excited by a given energy field of pre-defined characteristics. Generic or random field excitations do not optimally excite a given particle. The field excitation of a nano-particle is considered to be the "input energy" or "input driving function" of the system. In general, the "input energy" is converted by the nano-particles to an "output energy" which is a thermal output.

Operation of the Body Cavity Cancer Treatment Apparatus

Figure 1B:
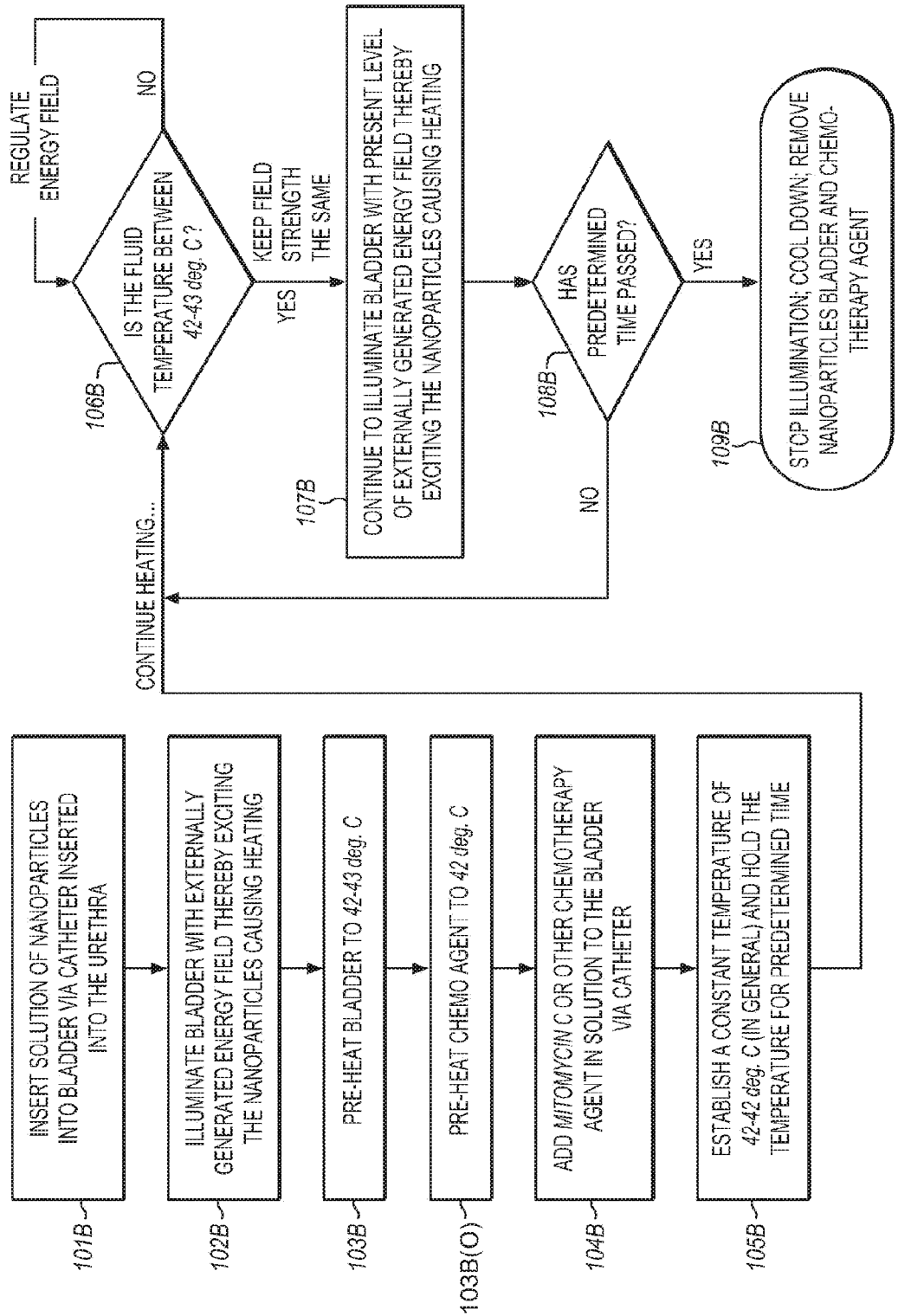

FIG. 1A illustrates in flow diagram form the typical operation of the present body cavity cancer treatment apparatus 40, while FIG. 1B illustrates in flow diagram form the typical operation of the present body cavity cancer treatment apparatus 40 as implemented in a bladder cancer treatment protocol. The present body cavity cancer treatment apparatus 40, as described herein, is used to generate the magnetic fields used in these treatment protocols.

At step 101A of FIG. 1A, a solution of nano-particles is inserted into the target body cavity by whatever technique is appropriate for use by medical personnel. At step 102A, the body cavity is illuminated by the application of an externally generated energy field, such as a magnetic field generated by the body cavity cancer treatment apparatus 40 of FIGS. 2-5, 6A, and 6B. The energy field is maintained by the body cavity cancer treatment apparatus 40 to slowly heat the body cavity at step 103A to a predetermined temperature. At step 104A, one or more chemotherapy agents are added to the body cavity, with the chemotherapy agent optionally being preheated to a predetermined desired temperature at step 103B. At step 105A, the body cavity cancer treatment apparatus 40 establishes a constant selected temperature in the body cavity and/or chemotherapy agent by the energy controller 62 regulating the applied energy field via control computer 409, waveform sources 403, 601, amplifier 404 and current sense circuit 614. The process then advances to steps 106A-108A where the energy controller 62 of the body cavity cancer treatment apparatus 40 tests, via temperature sensors 616 or 617 and control computer 409, to determine whether the temperature of the body cavity/chemotherapy agent is within predetermined limits and, if not, regulates the intensity of the magnetic field to achieve the desired temperature. This process of maintaining the desired temperature continues for a predetermined time until the energy controller 62 of the body cavity cancer treatment apparatus 40 at step 108A computes that the predetermined time has elapsed, at which point, processing advances to step 109A where the magnetic field is removed, the body cavity and chemotherapy agent are allowed to cool and the nano-particle solution and chemotherapy agent are typically removed from the body cavity.

Alternatively, at step 110A, a mixture of a solution of nano-particles and one or more chemotherapy agents are added to the body cavity, with the mixture optionally being preheated to a predetermined desired temperature. At step 111A, the body cavity is illuminated by the application of an externally generated energy field, such as a magnetic field generated by the apparatus of FIGS. 2-5, 6A, and 6B. Processing then advances to step 105A, where the energy controller 62 of the body cavity cancer treatment apparatus establishes a constant selected temperature in the body cavity and/or chemotherapy agent and steps 106A-109A are executed as described above.

The treatment protocol is defined by the physician, who selects the time and temperature parameters. In addition, the solution of nano-particles and one or more chemotherapy agents may be combined, preheated, and then inserted into the body cavity. This reduces the treatment time and simplifies the process by implementing only one insertion step.

Treatment of Bladder Cancer

Figure 7:
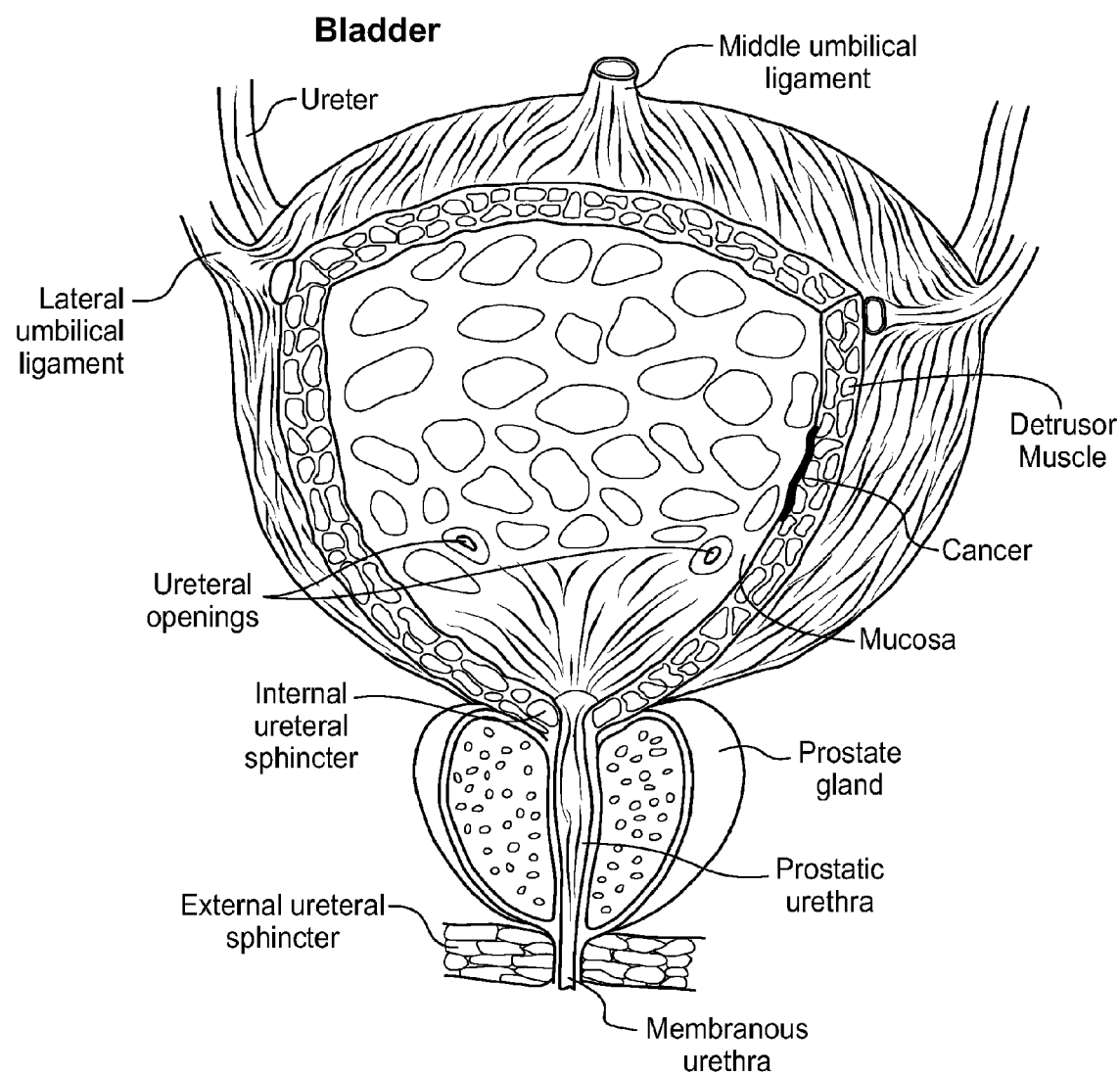
FIG. 7 illustrates a cross-section view of the human bladder, illustrating the major components thereof.

The process just described can be implemented for various body cavities as noted above and FIG. 1B provides additional details to the flowchart of FIG. 1A to show how this procedure can be customized for a particular body cavity and cancer type. In particular, FIG. 7 illustrates a cross-section view of the human bladder, illustrating the major components thereof. The detrusor muscle is a layer of the urinary bladder wall made of smooth muscle fibers arranged in spiral, longitudinal, and circular bundles. The bladder is held in place in the abdomen by the lateral umbilical ligament, and the middle umbilical ligament. The bladder receives urine via the ureter and expels urine through ureteral openings which feed the urethra. One form of bladder cancer, shown on FIG. 7, is termed "Non-Muscle Invasive Bladder Cancer" which is sited on the surface of the bladder interior and typically is no deeper than 500 microns in through the mucosa. Thus, the insertion of chemotherapy agents into the bladder ensures that the chemotherapy agents come into contact with the cancer.

When the bladder is stretched, this signals the parasympathetic nervous system to contract the detrusor muscle. This encourages the bladder to expel urine through the urethra, which passes through the prostate gland. For the urine to exit the bladder, both the autonomically controlled internal urethral sphincter and the voluntarily controlled external urethral sphincter must be opened. Problems with these muscles can lead to incontinence. If the amount of urine reaches 100% of the urinary bladder's capacity, the voluntary sphincter becomes involuntary, and the urine is ejected instantly. The urinary bladder usually holds 300-350 ml of urine. As urine accumulates, the wall of the bladder thins as it stretches, allowing the bladder to store larger amounts of urine without a significant rise in internal pressure.

The urge to urinate usually starts when the bladder reaches around 25% of its working volume. At this stage it is easy for the subject, if desired, to resist the urge to urinate. As the bladder continues to fill, the desire to urinate becomes stronger and harder to ignore. Eventually, the bladder will fill to the point where the urge to urinate becomes overwhelming, and the subject will no longer be able to ignore it.

The process just described can be implemented for various body cavities as noted above and FIG. 1B provides additional details to the flowchart of FIG. 1A to show how this procedure can be customized for a particular body cavity and cancer. Such customization obviously can be effected for any specific body cavity and cancer type.

At step 101B of FIG. 1B, a solution of nano-particles is inserted into the bladder by passing a catheter through the urethra, with the volume of fluid being selected to not fill the bladder, leaving room for the chemotherapy agent and normal urine production during the treatment timeframe. At step 102B, the bladder is illuminated by the application of an externally generated energy field, such as a magnetic field generated by the body cavity cancer treatment apparatus 40 of FIGS. 2-5, 6A, and 6B. The energy field is maintained to slowly heat the bladder, via the illumination of the nano-particles, at step 103B to a predetermined temperature, which is typically 42° C.-43° C., prior to the addition of a chemotherapy agent. At step 104B, one or more chemotherapy agents, such as Mitomycin-C are added to the bladder, with the chemotherapy agent optionally (step 103B (O)) being preheated to a predetermined desired temperature, which is typically 42° C. At step 105B, the energy controller 62 of the body cavity cancer treatment apparatus 40 establishes a constant selected temperature, which is typically 42° C.-43° C., of the fluid located in the bladder and the surrounding tissue for a predetermined time. A fiber optic thermal sensor 617 can be used with a computer-controlled algorithm 409 to manage and adjust the applied field strength via a feedback control signal 602 applied to the amplifier 404. The process then advances to steps 106B-108B where the energy controller 62 of the body cavity cancer treatment apparatus 40 tests to determine whether the temperature of the bladder/chemotherapy agent is within predetermined limits and, if not, regulates the intensity of the magnetic field to achieve the desired temperature. This process of maintaining the desired temperature continues for a predetermined time, typically 60 minutes, until the body cavity cancer treatment apparatus 40 at step 108B computes that the predetermined time has elapsed, at which point processing advances to step 109A where the magnetic field is removed, the bladder and chemotherapy agent are allowed to cool, and the nano-particle solution and chemotherapy agent are typically removed from the bladder by urination or flushing.

In some situations, it may be desirable to not have the nano-particles touch or come into contact with human tissue, for example, the bladder interior lining (mucosa). At the same time, it is still desirable to heat the interior of the bladder (or human tissue) to enhance the effectiveness of the chemotherapy agent or radiation, either or both intended to kill harmful cancer and cancer cells. In the case of bladder cancer, it is desirable to enhance the efficacy of chemotherapy agents such as Mitomycin C. An alternative to the procedure described above is the infusion of the chemotherapy agent into the bladder and the insertion of a "balloon" into the bladder. By using a balloon-based catheter assembly, the nano-particles can be both heated and still retain their physical isolation from human tissue—the bladder lining. The balloon molds to the exact shape of the bladder, so nano-particles in a solution are put into the balloon, inflating the balloon and forcing the chemotherapy agent into the space between the balloon and the walls of the bladder. The solution of nano-particles in the balloon is heated via the application of an illumination field. Alternatively, a fluid solution can be circulated through the catheter and into/out of the balloon, without the use of the nano-particles, to maintain the temperature of the chemotherapy agent in the bladder. The generated heat is transferred to both the bladder wall and the chemotherapy agent. At the end of the remaining portion of the procedure as noted above, the nano-particles are removed from the balloon and then the balloon is removed from the inside of the bladder, as is the chemotherapy agent.

Balloon Catheter Process Details

Figure 17A:
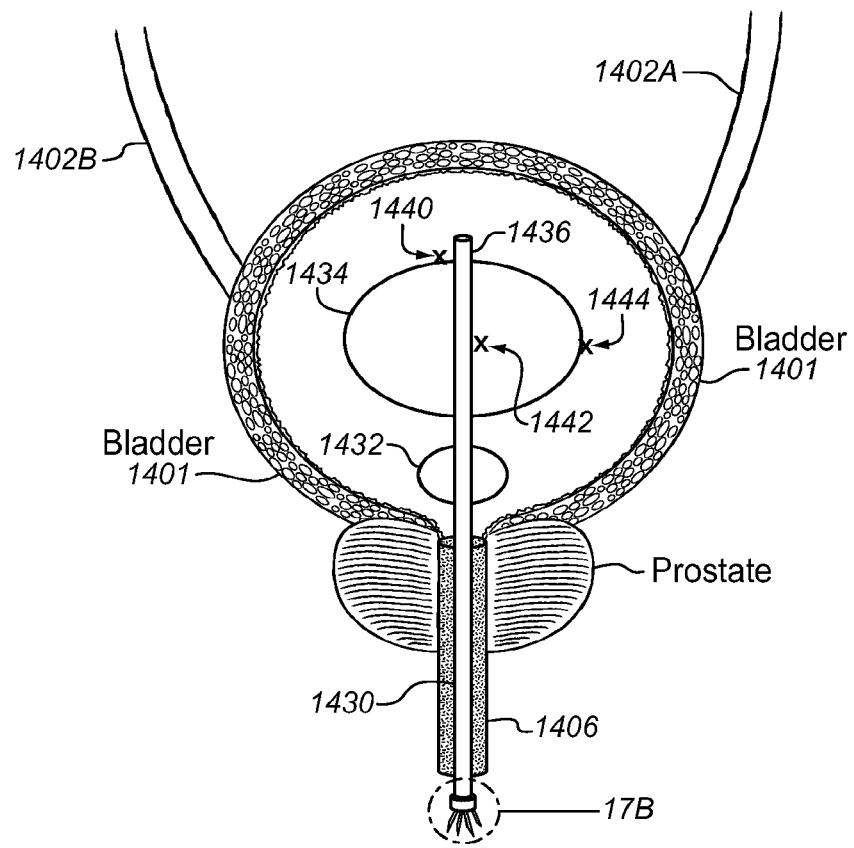
FIGS. 17A and 17B depict a catheter in a human bladder with associated catheter and human anatomy descriptions.
Figure 17B:
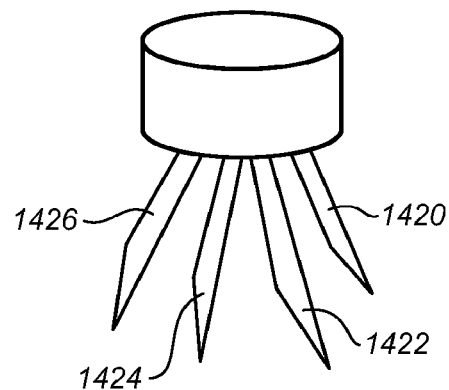

FIG. 17 shows a human bladder 1401 with a catheter 1430 already inserted into the bladder 1401. Catheter assembly (1430, 1432, 1434, 1436) is inserted into bladder 1401, which is connected to the kidneys (urine flowing into the bladder 1402 via ureters 1402A and 1402B), with the urethra 1406 being the means for draining the bladder 1401 (via urination) as well as a passageway for inserting the catheter assembly. The catheter 1430 has holes or tubes along its length which are called lumens. These lumens are in the cross section of the tubular portion of the catheter 1430. This particular catheter has four sets of lumens; the number of lumens is generally restricted only by the size of the catheter containing the lumens. The sizing of the catheter is measured in units termed "French" and, for human bladder use, the catheter is typically between 18 to 24 French. A larger French number means the catheter has a larger diameter.

Catheters are often constructed of extruded silicone or latex materials (the shaft is 1430, 1436 which is equipped with lumens 1420, 1422, 1424, 1426). The balloons (1432 and 1434) are often made via a "blown" methodology. Together, the extruded shaft 1430 plus the balloons 1432, 1434 are constructed to make the entire catheter assembly. Thermocouples 1440, 1442, and 1444 are added to enable a temperature control feedback mechanism to the energy controller 62 for managing the strength of the magnetic field, which in turn controls how warm the nano-particles get. For example, input lumen 1426 is connected to the output 1436 which is located at the tip of the catheter 1430 above the large balloon 1434. This particular lumen assembly is used to put fluid into or to take fluid out of the bladder 1401. At the beginning of the procedure, lumen pair 1426 could also be used to remove any excess urine and then, prior to the procedure starting it could be used to insert Mitomycin C, a chemotherapy agent, into the bladder 1401.

The combination of both heat and the chemotherapy agent are the basis of a treatment protocol that has significantly higher efficacy than just a chemotherapy agent alone (as is now practiced by urology oncologists). By adding heat to the bladder tissue and cancer for a nominal one hour treatment time frame, the efficacy of Mitomycin-C to treat bladder cancer is quite dramatic—the ten year complete cure rate is increased from 15% to upwards of 53%.

Lumen pairing, 1424 (input) to 1434 (output into the larger balloon 1434), is used for instilling nano-particles into the balloon 1434. One advantage of using a balloon to contain the nano-particles is that the ureters 1402B and 1402A do not dilute the nano-particle concentration with urine from the kidneys. Thus, the nano-particle concentration is constant and it simplifies the heating control algorithm.

The Mitomycin-C (chemotherapy agent) is instilled via lumen 1426 and output 1436 directly into the bladder 1401. Lumen 1422 is used to inflate the small balloon 1432, typically with air; the purpose of this small balloon 1432 is to keep the catheter 1430 seated in the bladder 1401 during the treatment time frame. It is desirable to keep the larger balloon 1434 off of the bladder wall since this balloon 1434 is the heat source and it is desirable to not have the warm balloon surface touching the bladder wall to prevent either burns or excessive heating.

In this example, lumen 1420 is used to link three thermocouples 1440, 1442 and 1444 which sense the temperature in three different locations to the energy controller 62. Thermocouple 1440 senses the temperature of the fluid (Mitomycin-C with some urine) in the bladder 1401 while thermocouple 1442 senses the temperature in the center of the balloon 1434 which holds the nano-particles (it is fed thru lumen 1420). It is important to check the temperature at the center of the balloon 1434 because it enables the energy controller 62 to know what the maximum temperature is and then what the thermal gradient is across the balloon 1434. The thermocouple 1444 is located on the outer edge of the balloon 1434 and is used to ensure that the external balloon temperature is safe for the bladder 1401 should it ever touch the bladder wall. Mathematically, the temperature difference between thermocouples 1442 and 1444 can be determined, as a gradient, and this calculation can be compared to measured temperatures as an error check to ensure no thermocouples are mis-reporting their data. Typically, thermocouple 1444 measures 2° C.-4° C. warmer than the temperature on the bladder wall. The thermocouples used are typically fiber optic-based, using a Gallium Arsenide (GaAs) crystal which vibrates at a given frequency for a given temperature. This vibration frequency is sensed and is then converted to a temperature measurement and reported to the systems electronics in a temperature to magnetic field strength feedback loop. Fiber optic sensors are important since they are not affected by the presence of a magnetic field which is used to excite the particles in Brownian motion thereby causing frictional based heating.

Figure 18:
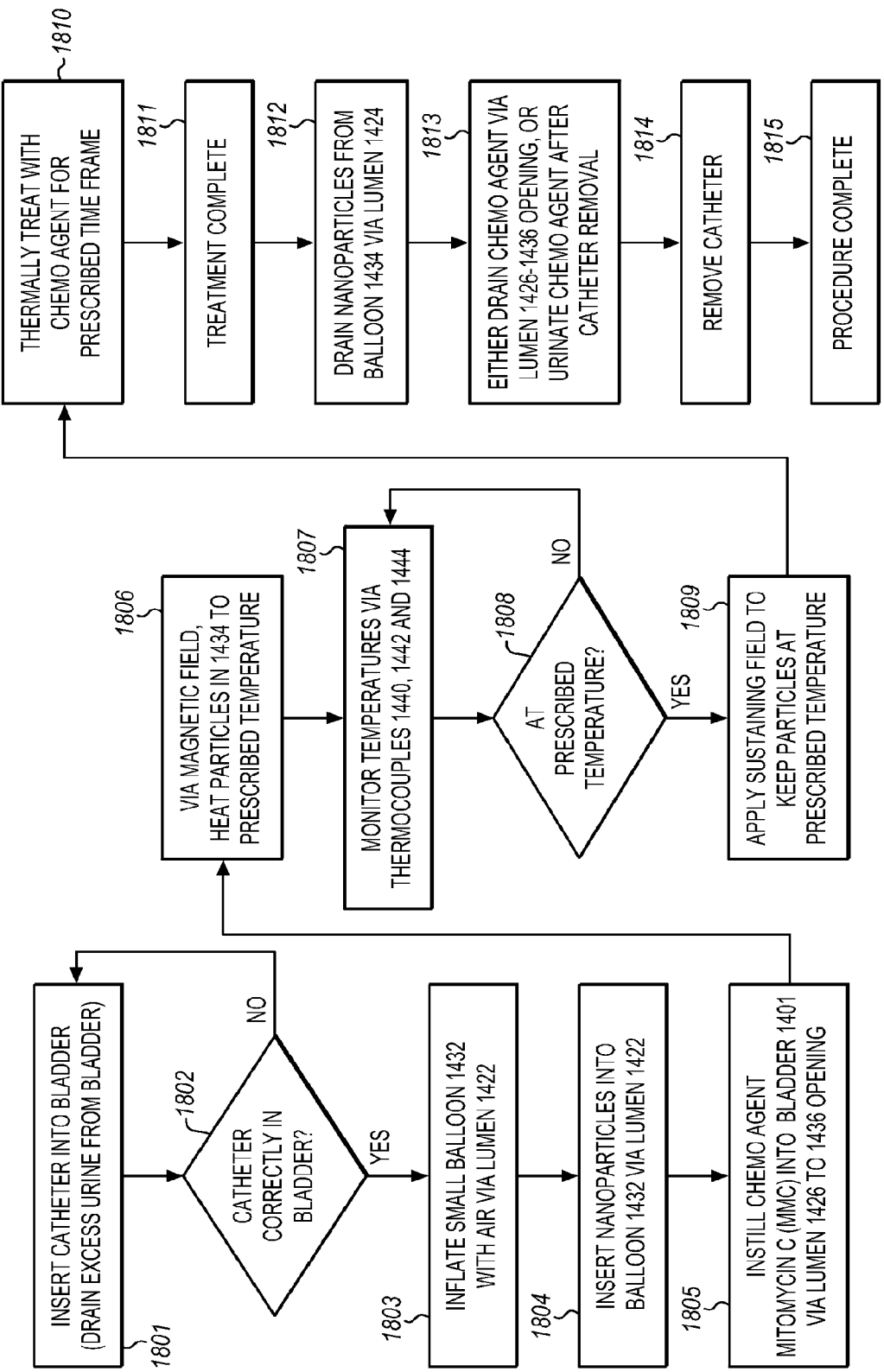
FIG. 18 describes in flowchart form the process of using a catheter to instill particles into the bladder while retaining particle isolation from the bladder itself.

FIG. 18 illustrates in flowchart form one process for nano-particle heating. At step 1801, the catheter 1430 is inserted into the bladder 1401 and at step 1802 it is determined to be positioned in the correct location in the bladder 1401. At step 1803, the small balloon 1432 is inflated (typically with air); this small balloon 1432 keeps the catheter 1430 properly installed as well as helping to keep the large balloon 1434 holding heated nano-particles from touching the bladder interior lining.

This treatment is largely for Non-Muscle Invasive Bladder Cancer (NMIBC) which is polyp-like and grows inward into the bladder wall of the bladder 1401 and, in general, has a stalk-like structure. Current thermal projections indicate that the thermal treatment needs to penetrate only 0.5 mm into the bladder wall to treat Ta and T1 NMlBC types of bladder cancers. At step 1404, nano-particles are inserted into the larger balloon 1434 via lumen 1424. At step 1805, the chemotherapy agent, such as Mitomycin C, is inserted into the bladder 1401 directly via lumen 1426 to opening 1436. Next, the magnetic field is applied as previously described herein. At step 1806, the nano-particles are heated in balloon 1434 in the prescribed manner. The overall system temperatures are monitored by the energy controller 62 via thermocouples 1440, 1442 and 1444 at step 1807. Note that either or both the Mitomycin-C and the nano-particles can be pre-heated to the nominal body temperature of 37° C. prior to insertion via catheter 1430 as described above. This pre-heating of the two materials shortens the overall procedure time-frame since they are at body temperature at insertion.

At step 1808, the energy controller 62 checks one or more of the thermocouples to ensure they are at the proper operating temperature and if too warm, the feedback to the amplifiers 404 feeding current into the coils 601, 602, is turned down which further lowers the magnetic field generated thereby reducing the heating rate. Once at the desired operating temperature, at step 1809, the magnetic field is managed to keep the nano-particles at the prescribed temperature, typically 42° C.-43° C. for low temperature non-ablative therapy.

At step 1810 the treatment protocol, using heated nano-particles and chemotherapy agent, is managed for the doctor-prescribed timeframe, but typically for an hour at the therapeutic temperature. It is believed that a 1° C. temperature increase can reduce the treatment time frame by ½ and a 2° C. increase in temperature is a ¼ reduction in heating time frame. However, the pairing of temperature with time is to be determined and is ultimately the responsibility of the treating physician.

At step 1811, the treatment is done and the "reverse" process is now effected. At step 1812, the nano-particles are drained out of balloon 1434 via lumen 1424. And at step 1813, the chemotherapy agent can be drained via lumen 1426 or the catheter 1430 can be pulled and the patient urinates out the chemotherapy agent. This is how the chemotherapy agent is removed today. There is an advantage to removing the chemotherapy agent via catheter 1430 due to how caustic the chemotherapy agent is to the urethra and its lining. At step 1814, the catheter 1430 is removed and at step 1815 the procedure is completed.

Cancer Cells and Hyperthermia

For cells that are dividing, four (4) phases exist—M-phase, $G_1$-phase, S-phase and $G_2$-phase—with radiation and hyperthermia each affecting different phases. Hyperthermia is most sensitive in the last half of the S-phase, DNA reproduction. The next cellular phase which hyperthermia impacts are the M-phase, cell division. However, radiation sensitivity is high in the M-phase (cell division) but low in the S-phase (DNA reproduction). Thus, hyperthermia is complimentary with radiation—particularly for the S-phase, which is the DNA reproduction phase. That is why low temperature hyperthermia (LTH) is so effective when combined with radiation. As previously mentioned, PARP inhibitors affect the DNA repair stage, similarly where hyperthermia works and, hyperthermia enhances the effectiveness of chemotherapy at an effectiveness doubling rate for every degree above body ambient.

The nano-particles that heat in a magnetic field must exhibit magnetism and are generally ferromagnetic in nature. Materials such as magnetite $Fe_3O_4$ and maghemite $Fe_2O_3$, when produced in nanometer sizes, will heat in magnetic fields of time-varying nature. These AC or alternating current magnetic fields are typically in the kilohertz frequency range but can also be in the megahertz range. For the preferred Brownian heating mode, the optimal frequency range is 30,000 to 100,000 hertz (30-100 KHz). The particle sizes are sufficiently small in diameter to be characterized as predominantly a single domain.

Magnetic excitation is via an alternating current (AC) driven, where the change of the phase of the wave going from positive to negative to positive (and so on) causes changing magnetic alignments in the nano-particles which in turn cause heating. The changing magnetic alignment causes a portion of the induced energy to be converted as heat (by the nanoparticles). The two forms of magnetic heating involve: one, friction based heating created by the nano-particles' movement with respect to the cytoplasm (for instance Brownian) and, two, heating which is magnetic domain-based (Neel), where the nano-particles are stationary and the magnetic domains in the nano-particle are changing. Depending on the particle size relative to the excitation frequency, the heating could involve both Brownian and Neel modes.

The first, friction based, is called Brownian heating and the nano-particle physically rotates, causing mechanical friction-based heating. Because the nano-particle is physically rotating, there is a relaxation time that is optimal for maximal nano-particle heating where the relaxation time is related to both the nano-particle size and the excitation frequency. This unique pairing of nano-particle size with frequency causes optimal heating. In this case, the nano-particle size, composed of the core plus any coatings, is called the hydrodynamic diameter, and it is this composite size that is important for Brownian heating. Additionally, the material's properties, such as magnetization and anisotropy, affect where and how well it heats.

The second method, where just the magnetic domains are changing, is called Neel heating. In this case, a very narrow size and corresponding frequency match enables heating; and, any slight changes in those parameters can cause the nano-particle to not heat at all. It is this very sensitivity that makes Neel heating the less preferred approach.

Other modes of magnetic nano-particle heating include hysteresis and Rayleigh, where these modes are usually reserved for significantly bigger particles, say greater than 50 nanometers in size. In single domain modes where the nano-particles are smaller (less than 50 nm in general) Brownian and/or Neel heating are preferred. Presently, the preferred magnetic field generation mechanism is a set of coils which projects magnetic fields into tumorous regions in which the fields create a uniform volume in the region where the cancer resides. Relatively uniform fields across a tumor are important for minimizing hot spots (we assume that nano-particle uptake is relatively uniform across a tumorous region).

The Treatment Table/Machine

FIGS. 2-4, 6A and 6B illustrate the body cavity cancer treatment apparatus 40 that is used to illuminate the patient with an externally generated magnetic field. Two coils 401, 402, positionable above and below the patient 407, create a magnetic field between the two coils 401, 402 which harmlessly passes through the body of the patient 407. This magnetic field excites the 20 nm nominal sized magnetite $Fe_3O_4$ nano-particles that have been inserted into the bladder cavity of the patient 407 and causes them to heat up, predominantly via Brownian excitation. Brownian heating is a result of the particles physically rotating at the rate of the excitation frequency, in this case, 40 KHz. The level of nano-particle heating is based on the level of electrical current in the coils 401, 402 which then produce a given magnetic field strength of a prescribed level.

Figure 3:
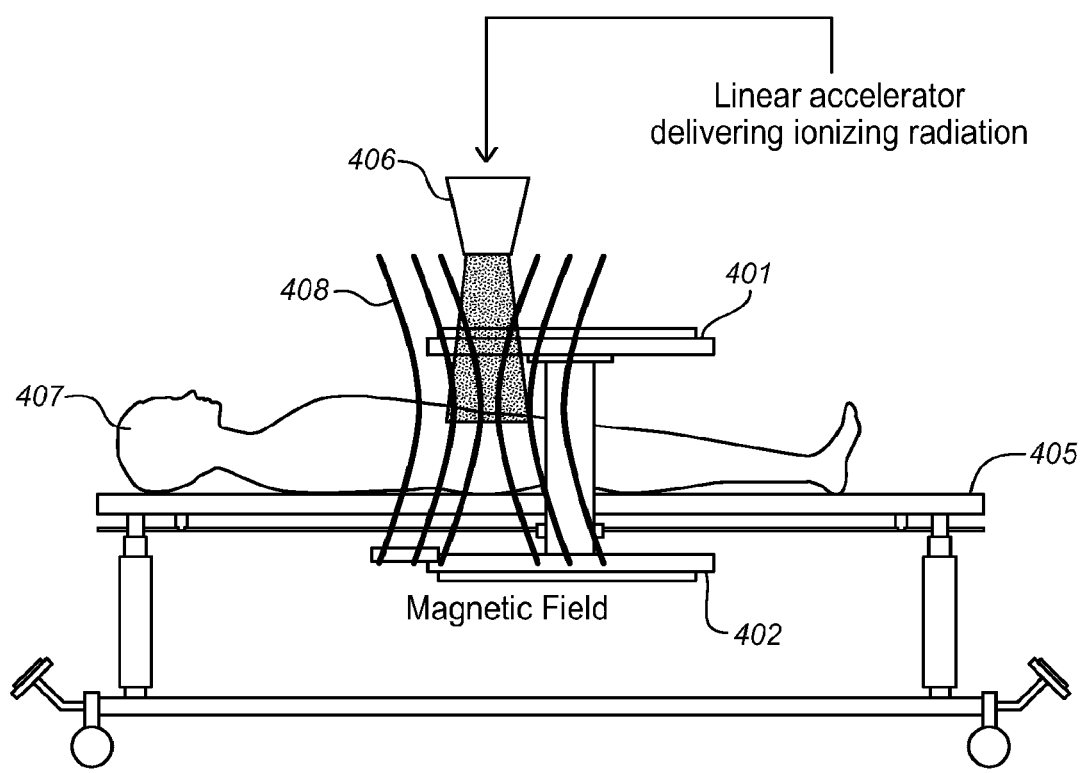
Figure 4:
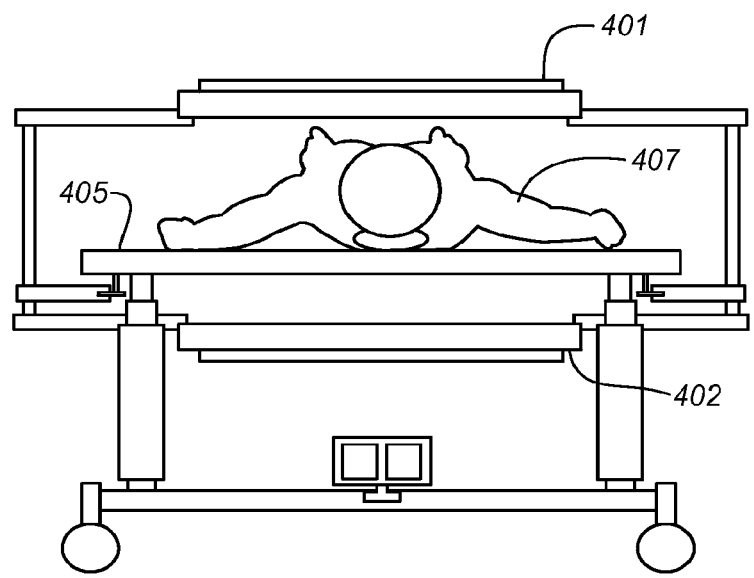

FIGS. 3 and 4 show how the open coil ring enables the passage of ionizing x-ray radiation 408 for an additional treatment protocol. Again, the preferred embodiment of the body cavity cancer treatment apparatus 40 is the generation of a magnetic field to illuminate magnetic field-susceptible nano-particles. However, an electric field with electric field particles or substances can also be used. As an example, Mitomycin-C is dipolar and may heat in an electric field. If so, this would remove the need for nano-particles.

Figure 2:
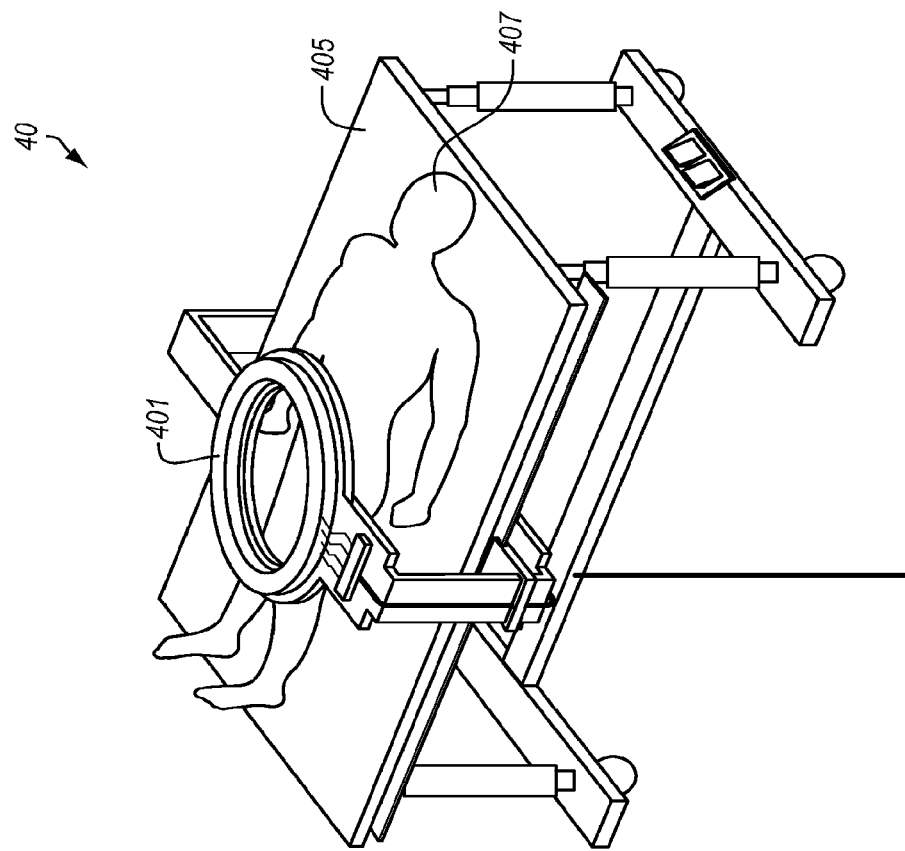
FIGS. 2, 3, 4 and 5 illustrate the apparatus that is used to illuminate the patient with an externally-generated magnetic field.
Figure 2:
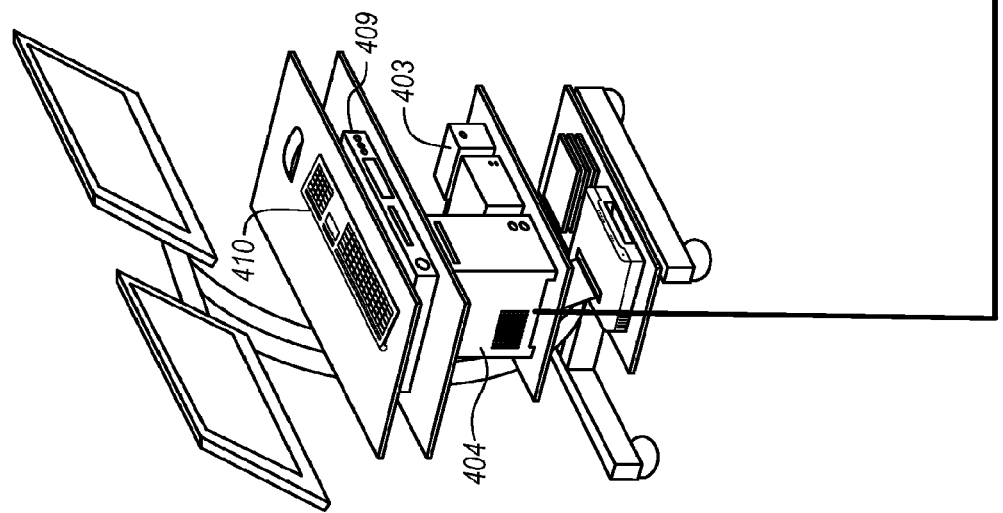
Figure 5:
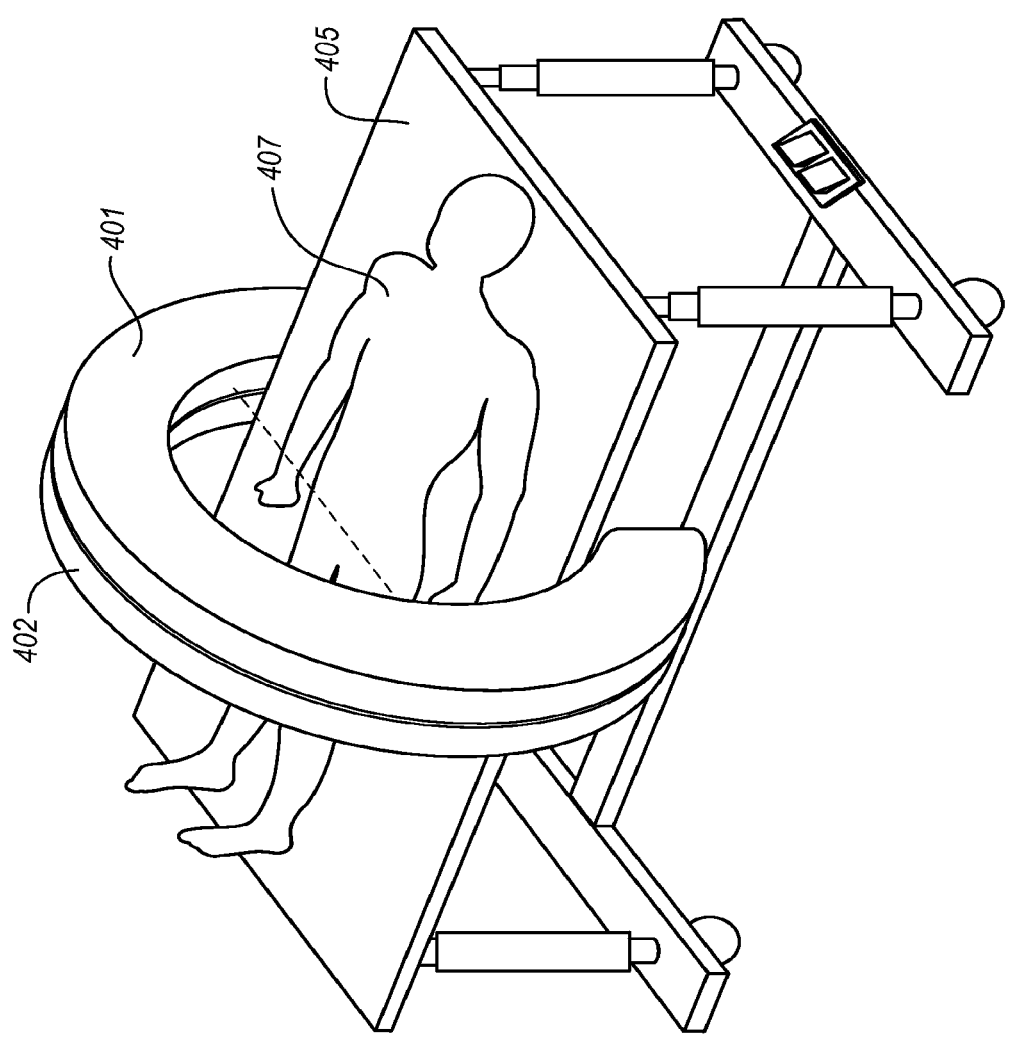

FIGS. 2-4 show a patient (living organism) 407 lying face up on table 405 with the coil assembly 401, 402 of the body cavity cancer treatment apparatus 40 sliding over the body 407 to optimally align the coil pair 401, 402 over the region of the patient's body to be illuminated (the region that contains nano-particles). Note that while not directly visible in this perspective of FIG. 2, there is a bottom coil 402 of the body cavity cancer treatment apparatus located under the table sliding in concert with the upper coil 401 going over the patient 407. FIG. 6B illustrates a cross-section diagram of the body cavity cancer treatment apparatus, which shows the two coils as well as the target area where the magnetic field is focused on the patient who is on the table as well as the surrounding area of reduced magnetic field and a surrounding buffer area. This conceptualization of the body cavity cancer treatment apparatus 40 uses a toroid shaped coil having a coil diameter of 60 centimeters, or 23.6 inches. In practice, the coils 401, 402 can be of any size or even shape, such as square. Other coils 401, 402 could also be added in an orthogonal plane as shown in FIGS. 4 and 5 (as the sole coil) to enhance the size of the uniform heating region. The "first winding, upper coil" to "first winding, lower coil" spacing is 30 cm in this concept (which can be increased to accommodate larger people). An increased spacing of the coils 401, 402 would either mean a larger coil diameter or more drive current for the existing coil diameter (to compensate for the fields falling off or being "stretched" by increasing the spacing) to produce the same magnitude energy field. Alternatively, lower field strength can be used with the caveat that slightly more time is required to reach the target temperature.

Figure 6A:
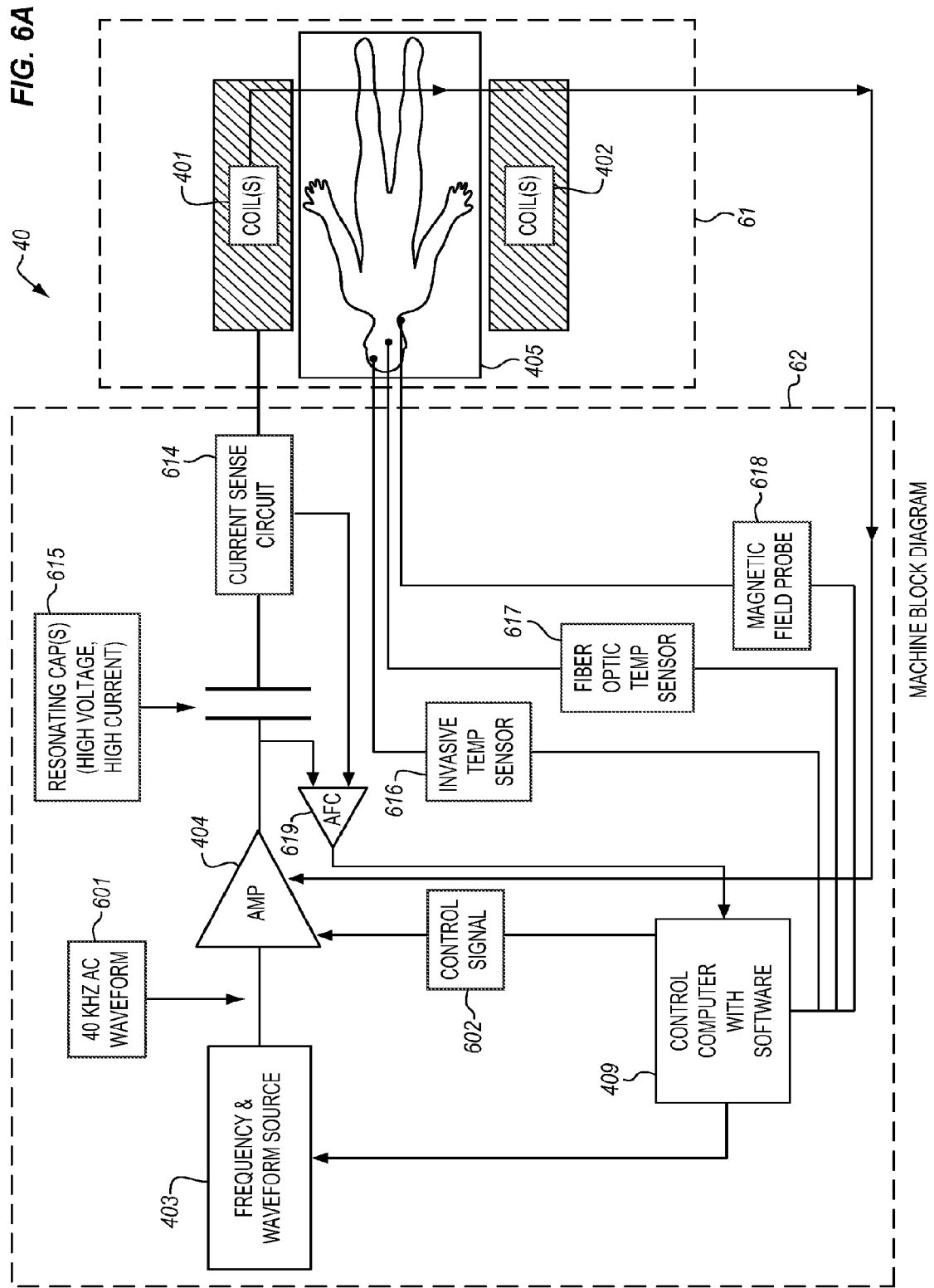
FIGS. 6A and 6B illustrate a block diagram of the body cavity cancer treatment apparatus.
Figure 6B:
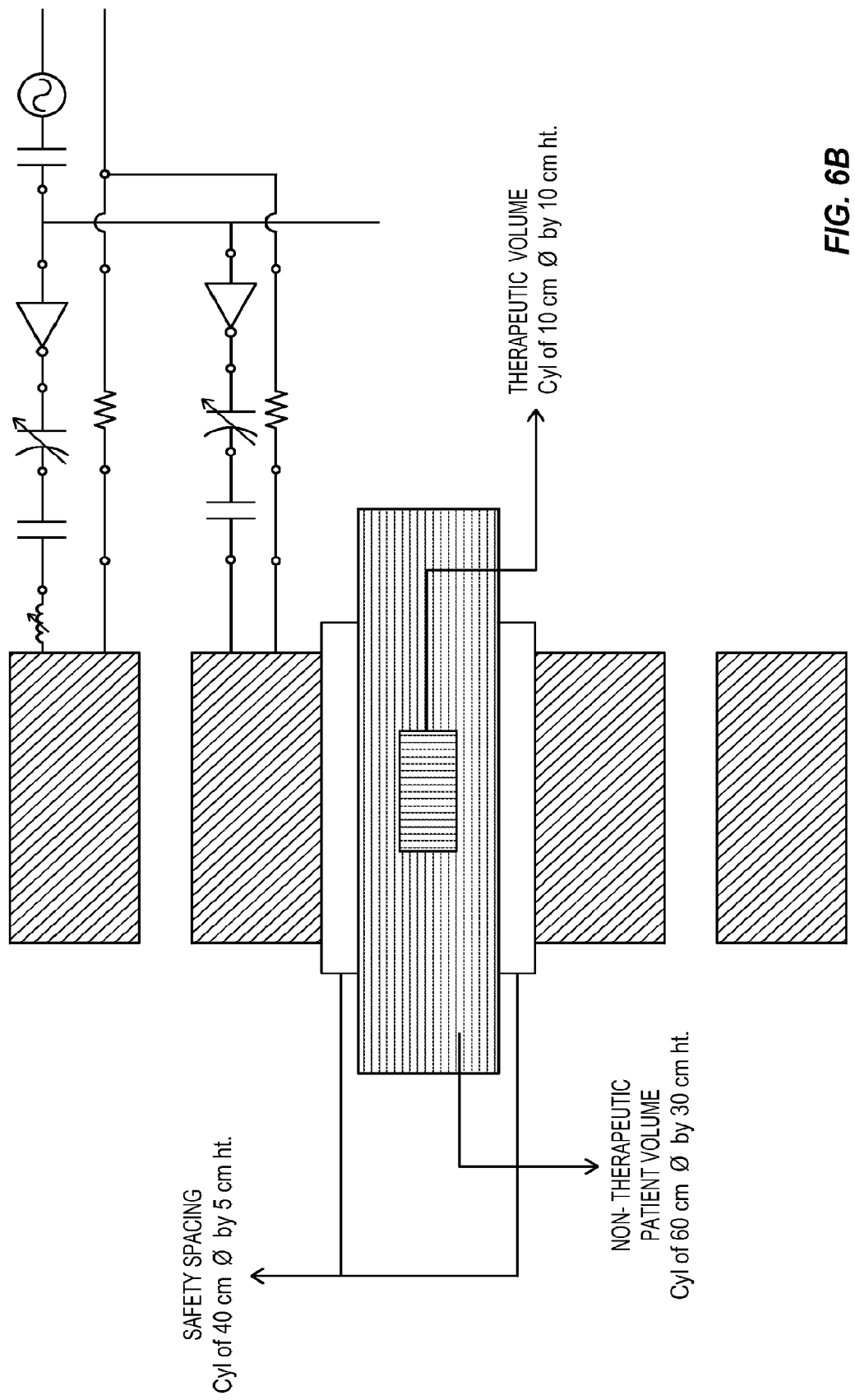

FIG. 2 also shows an implementation of the body cavity cancer treatment apparatus 40 which has an electronics equipment rack which contains the signal source 403, signal amplifier 404, control computer 409 with software, user input keyboard 410 with GUI touch screen and fiber optic temperature measurement system 617, as also illustrated in schematic form in FIGS. 6A and 6B. An AFC circuit 619 is also provided to bring energy controller 62 back to resonance by sensing the phase between the voltage and the current and selecting a new excitation frequency to get back to the resonance driving frequency. The control computer 409 is used by the physician to select the characteristics of the generated energy field, as described above, to match the characteristics of the nano-particles that are inserted into the cavity, as well as to define the treatment protocol: temperature, duration, and heating profile. Alternatively, invasive temperature sensor 616 would have sensors on the body of the patient 407. Separately, for a bladder heating assembly using a Foley catheter to administer both the nano-particles and the chemotherapy agent such as Mitomycin-C, a fiber optic temperature probe can be inserted into the bladder cavity to measure the treatment temperature of the fluid in the bladder. Finally, a magnetic field probe 618 can be used to measure the energy field within the cavity.

The magnetic volumetric region of quasi uniform fields is on the order of 30 cm in body thickness dimension by an area of 35 cm in body width by 35 cm in body length, which is 11.8 inches in body thickness by 13.8 inches in body width by 13.8 inches in body length. Overall, this is 36,750 cubic centimeters of "uniform field" volume or 2,247 cubic inches of "uniform field" volume. It is believed that this uniform field volume is sufficient for virtually any type of regionally-located cancer that hasn't metastasized. These uniform field regions can be further seen in FIGS. 8, 9A and 9B where computer simulations show the expected magnetic field densities.

The coils 401, 402 of the body cavity cancer treatment apparatus 40 require other passive components in order to allow them to efficiently and safely work with a given amplifier design. Most amplifiers 404 prefer a "real" input in terms of the input impedance presented by the coil load. To realize "real" impedance in the body cavity cancer treatment apparatus 40, the inductive reactance of the coil must be matched with an equivalent series connected capacitor 615 to cancel out the reactive voltages. This is to stay in compliance with the amplifier's operating requirements. As shown in FIG. 6A, the coils 401, 402 and capacitor 615, connected in series, realize a series LC circuit which is resonant at the desired illumination frequency. The series LC circuit, at the resonant illumination frequency, has zero reactance and only the AC resistance of the coils 401, 402 and the ESR (equivalent series resistance) of the capacitors 615.

At resonance, what are left in the coils are AC resistive losses. The capacitors 615 have an equivalent series resistance, which is frequency dependent; in order to get the equivalent series resistance low, a number of capacitors need to be put into a parallel configuration (if the capacitors are at the system input); or, alternatively, as shown in FIG. 6B, the capacitors are distributed into the windings of the sub-coils. Again, the "matching circuit" uses capacitors to cancel out the inductive reactance of the coil assembly in order to reduce the reactive voltage to "zero" at resonance. In addition, at least one capacitor per coil or sub coil, if broken into sub coils, should be a variable capacitor to make sure all of the coils are resonant at the same frequency. For a variety of reasons, the selected frequency of operation of the body cavity cancer treatment apparatus 40 is typically 40,000 hertz (40 KHz).

How the coil is wound and how the wires are juxtaposed to each other significantly affects the AC resistance or equivalent series resistance. This also affects the field strength generated for a given current into the coil windings. If a gap of 0.6 to 0.75 inches (around 1 cm) is placed between the axial windings, the equivalent series resistance can be significantly reduced. Presently, at 77 amps RMS of drive current, the AC resistance of the coil is around 0.3 ohms at 40 KHz. Radially, the wires (or rather the insulation of the wires) can be touching without much effect on a person's skin.

Other coil related issues must be managed, such as ensuring that corona inception is not possible at the given air pressure and temperature. Corona inception is where the voltage gradient or field strength is of a sufficient level, say 24.1 Kv per cm, at 6,000 feet altitude and 40° C.—if the voltage gradient on the outer edge of the wire insulation or say between the edges of two wires' insulation is greater than 24.1 Kv/cm—then a corona inception is possible. Corona is essentially the breakdown of the air gap and is evidenced by purplish or orangish light, a staccato-like sound and then eventually a voltage arc.

Selections of the insulation, the spacing, the number of turns, how the coil is wound and so on all affect the likelihood or risk of corona. One key method of reducing the level of the voltage gradients is to add air gaps between the wires in the axial direction (direction of the human body 407 in FIG. 5) and to break up the coil up into two coils, separated by both air and a plastic dielectric. These two sub-coils are not spaced sufficiently to garner the Helmholtz condition, described below.

The B field and the H field are vectorially parallel to the human 407. The nominal treatment volume is on the order of a cylinder 10 cm in radius and about 20 cm long. The length of the uniform field volume is dependent on how far apart the two sub coils are spaced (again, not at a Helmholtz condition). This field volume is sufficiently large to have a uniform field for the treatment volume (particle balloon volume) and sufficiently large enough to not cause difficulty in centering this region onto the patient. There may be some eddy current heating advantages to the coil body relationship as shown in FIG. 5. This is due to the volume-based integral of field lines being captured by the body—a Helmholtz design, where the two coils are farther apart, and cause more lines of flux to be captured by the body 407—hence have higher unintentional eddy current. The only thing the Helmholtz Condition creates is a uniform field for some prescribed volume. There are other coil configurations that do this as well—Maxwell, Merritt, etc.—some have two coils, the Merritt has three coils and others have four coils. Most are axial—that is, the body is inside the coil like an MRI. The Helmholtz coil architecture is side to side, but could be axial say for an arm or head/neck cancers.

The system shown in FIG. 5 has two coils, spaced tighter than a Helmholtz version, for very specific design reasons: managing the induced voltages and field gradients of the wire-to-wire and sub-coil to sub-coil to levels that are below air-based corona inception and wire insulation failure. Spacing the coils electrically creates "two" coils from a circuit perspective, and each coil now has half the voltage across it versus having one coil with all of the voltage across it. This architecture has one coil, one capacitor with the second coil and the second capacitor, to resonate the system and to lower the voltages for both the capacitors and the individual coils.

When you have a Helmholtz pair of coils, the spacing between the coils is one half the diameter of the coils. If this were done for bladder cancer, the coils get very large (side to side) due to the minimum spacing for large people. When the coils get very large, it imposes magnetic lines of flux on greater portions of the body, and hence the system has higher eddy current heating of healthy tissue. This is another design reason why side-to-side coils are not preferable for bladder cancer with a Helmholtz design. The axial coil as shown in FIG. 5 has lower eddy current heating of healthy tissue.

Litz Wire

For wire that is carrying an AC current, an effect called "skin effect" occurs, which means that only the narrow outer core of a solid wire carries the current. Thus, the current-carrying cross section has been dramatically reduced from the full wire area to a small height donut; therefore, the AC resistance can be significantly higher than the DC resistance. Special wire is used in the body cavity cancer treatment apparatus to minimize this effect.

In addition, a second effect, called "proximity effect" happens when wires carrying current are placed near each other. The wires effectively couple to each other and subsequently reduce the physical region where current is being carried in the wires. This physical effect increases the AC resistance of the coil assembly. Again, like for "skin effect", special wire is used to manage the issues of "proximity effect".

The AC resistive loss of the wire used to implement the coils in the body cavity cancer treatment apparatus, caused by "skin effect", "proximity effect" and $I^2R$ losses in the windings creates a voltage across the windings. To minimize this resistance and hence voltage, special wire called Litz Wire is used. Litz Wire has upwards of over 1,000 enameled individual conductors inter-wound and inter-woven, depending on frequency selected and maximum current used. At 30,000 Hz, the loss of Litz Wire at lower AC frequencies is virtually the same as the DC loss—thus, we have overcome the negative issue of skin effect and proximity effect. At moderately higher AC frequencies, the losses are quite manageable and significantly lower than what they would be if Litz Wire were not used.

The Litz Wire used has 2,600 strands of enamel-insulated 36 gauge wire, where the individual strands are interwoven and the interwoven blocks are further woven. This interleaving of wires insures that no two wires are close to each other for any extended length. Braiding the wires into a structure where each strand spends an equal time in the center of the braid as all other strands helps to minimize both skin and proximity effect. Selecting the gauge of the strands, the number of strands, and other factors, is a design optimization process which optimizes AC losses, cost, usability, and so on.

However, the length of the wire in the coils of the body cavity cancer treatment apparatus is sufficiently long (400 to 420 turns with a 60 cm diameter) that the AC voltage across the coil at 40 KHz is quite high for higher drive currents, approaching tens of kilo-volts and higher. So, the coil windings need to be broken down into "sub-coils" either in the Z-direction or the X-Y direction. By breaking up the coils into sub-coils, the inductive reactance is lowered, and therefore the AC voltage at 40 KHz is lowered. In addition, by breaking up a single coil winding length into shorter lengths of wire (using sub-coils), the sub-coil resistances are in parallel and resistances in parallel are lower than their original individual values, if they are driven in parallel. In FIG. 5, the two coil halves are more easily seen; in this configuration, the material of the table needs to be magnetically transparent (i.e. no metal that has magnetization). Wood or certain plastics work to realize a magnetically transparent surface. When the coils are wound, the wire diameter is 0.476 cm with insulation thickness at 0.85 cm, putting the entire wire thickness (strands plus outer insulation) at just under an inch. From the mid-point of the winding, it is plus or minus 2 inches. This physical thickness changes the ideal field generation of the coil assembly and upwards of 10-15% of the theoretical coil field is lost due to the imperfect physical realization of the coil fields (i.e. the wires are not infinitely thin).

Coil Design Equations

The equations used to design the coils are ideal. When the wire cross section is no longer an infinitely thin current source, the coil becomes less efficient than pure theory. In addition, if the coils are separated by more than their nominal radius (R) separation, an additional loss occurs. These phenomena affect the overall gain of the coil system and fortunately can be predicted by computer modeling using Finite Element Modeling or FEM.

The Biot-Savart Law describes the magnetic fields produced by an AC current. The magnetic field is given by the variable "B" in A/m or tesla. A dual coil system is created by taking two single Bio-Savart equations.

$$B = (u_o)(n)(I)(R^2)/((R^2)+(x)^2)^{1.5} \text{ in tesla}$$

Or $$B = \frac{(u_o)(n)(I)(R^2)}{((R^2)+(x)^2)^{1.5}}$$

Where ($u_o$) is the permeability of free space and is 1.26 E-6 T*m/A (if you want A/m as the output, simply leave out $u_o$)

(R) is the radius in meters (I) is the current in amps (n) is the number of windings (x) is one half the spacing (divide actual coil separation by two, and that is "x")

With a one amp current and a one turn winding, for a coil system that has a separation of 0.1 meters with a radius of 0.1 meters, the field strength is calculated as 7.155 A/m. This is considered the gain of the single coil system. In contrast, if that 0.1 meter optimal separation is changed to 0.3 meters, the gain falls off to 1.71 A/m. These values are also shown in the plot of FIG. 5: 0.1 meter radius and 0.1 meter spacing; 0.1 meter radius and 0.3 meter spacing. Thus, keeping the coil separation distance close to the value of the coil radius is very important in order to not have a significant loss in maximal field strength.

This "perfect" spacing condition where the radius of the coil is the same as the distance between the coils is defined as the Helmholtz relationship. The Biot-Savart Law can be further reduced to the Helmholtz relationship if the spacing of the two coils is always the same as the radius of the coil(s). To get the Helmholtz coil equation, simply substitute x=R/2 in the aforementioned Biot-Savart equation and what results is this equation in A/m field strength:

Helmholtz Equation is:

$$A/m = (0.7155)(n)(I)/(R)$$

or . . .

$$\text{Helmholtz coil in } A/m = \frac{0.7155 * n * I}{R}$$

Proximity Effect

The proximity effect is an AC frequency-sensitive issue that occurs when wires are wound side-by-side, lying next to each other. The current for this pair of wires in close proximity tends to "bulge" near where the wires are "touching". This reduces the available cross section of the wire that is carrying current. For a single strand conductor, depending on its size in relationship to the skin depth, this additional loss (due to the current being concentrated in a smaller portion of the conductor area) can be significant.

The proximity effect gets more pronounced when the wires are layered on top of each other in addition to laying side-by-side—the more layers, the bigger the proximity effect. Depending on the variables involved, the AC to DC resistance change caused by proximity effect can be 50 to 100 or greater increase in the effective AC resistance over the DC resistance. Fortunately, all of this can be managed by proper selection of the sub-wire size, how many sub-wires are used in a single wire, how the wires making the windings are inter-woven, and so on.

If Litz Wire is used, which has tens to hundreds to a thousand strands of inter-woven wire, the combined effects of skin effect and proximity effect are less of an issue, especially if the sub-wire strand size is substantially smaller, meaning the ratio of wire size to skin depth is a small number. Litz Wire is a wire assembly especially made for higher frequency magnetic coil or transformer applications. The smaller gauge helps solve the frequency skin effect problem, and the many strands help solve the overall loss per unit length problem.

The key relationship to understand is the relative difference between the size of the conductor and the skin effect for the given frequency. Skin effect is the property of a conductor to carry most of the current in the outer "donut" of the wire's cross section. Thus, if the cross section of the wire is less than one skin depth, then the current is necessarily carried by the entire cross section of the given strand. Then, by using Litz Wire with many, many strands, the overall loss due to wire length can be managed back to a usable number.

The skin effect depth for 50 KHz is determined at the radial depth into the conductor where the current flow has fallen 1/c times that of the current on the surface of the conductor. For copper wire, at 100° C. (conservative value), having a Ur of 1 and a resistivity of p=2.3E-8 ohms-meter, the skin effect equation can be simplified to:

$$\text{Depth} = 7.6/\sqrt{j} \text{ in centimeters}$$

So, at 50 KHz, the skin depth is 0.034 cm (centimeters).

One Litz Wire configuration has its sub-wire strands as 38AWG, which has a diameter of 0.003965 inches or around 4 mils in diameter or 0.01007 cm (centimeters). Comparing the two values, skin depth vs. wire size, for the Litz Wire, we see that all of the current is carried by the wire's cross section. The wire radius divided by skin depth is 0.15. Thus, all of the current in the Litz Wire's sub-wire strand is carried in the entire cross section of the sub-wire in the Litz Wire assembly.

Figure 9A:
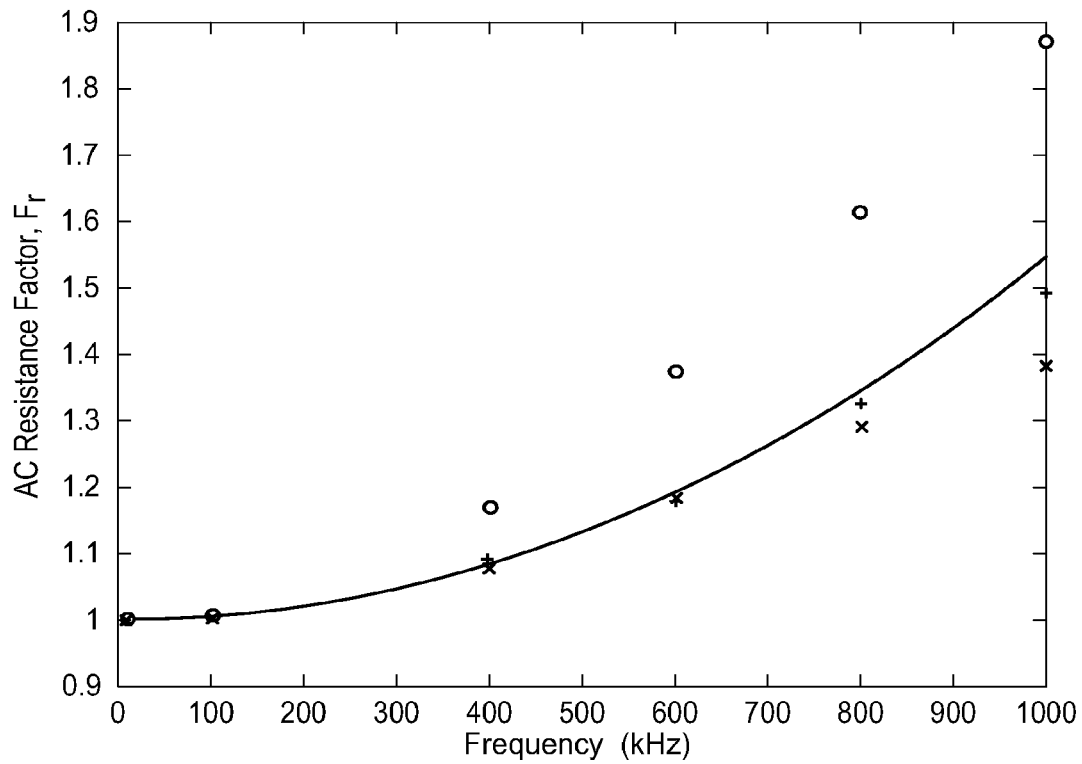
FIGS. 9A and 9B illustrate in graphical form a plot of the experimental resistance of the Helmholtz coil as a function of frequency.
Figure 9B:
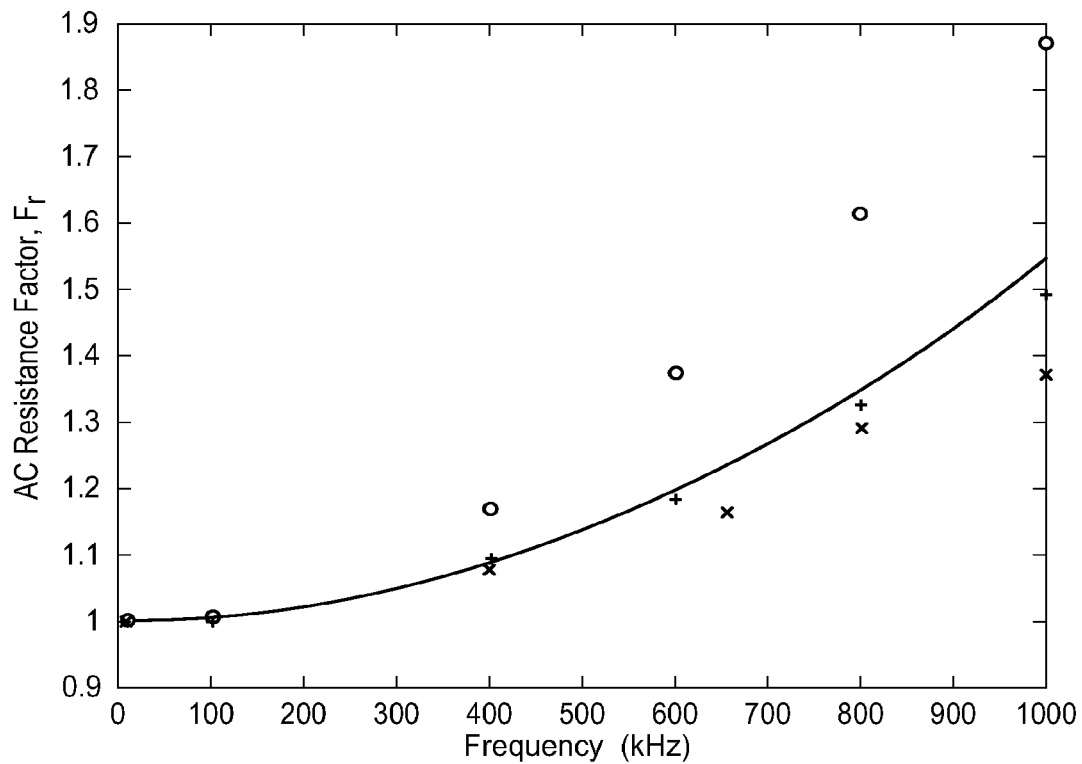
Figure 10:
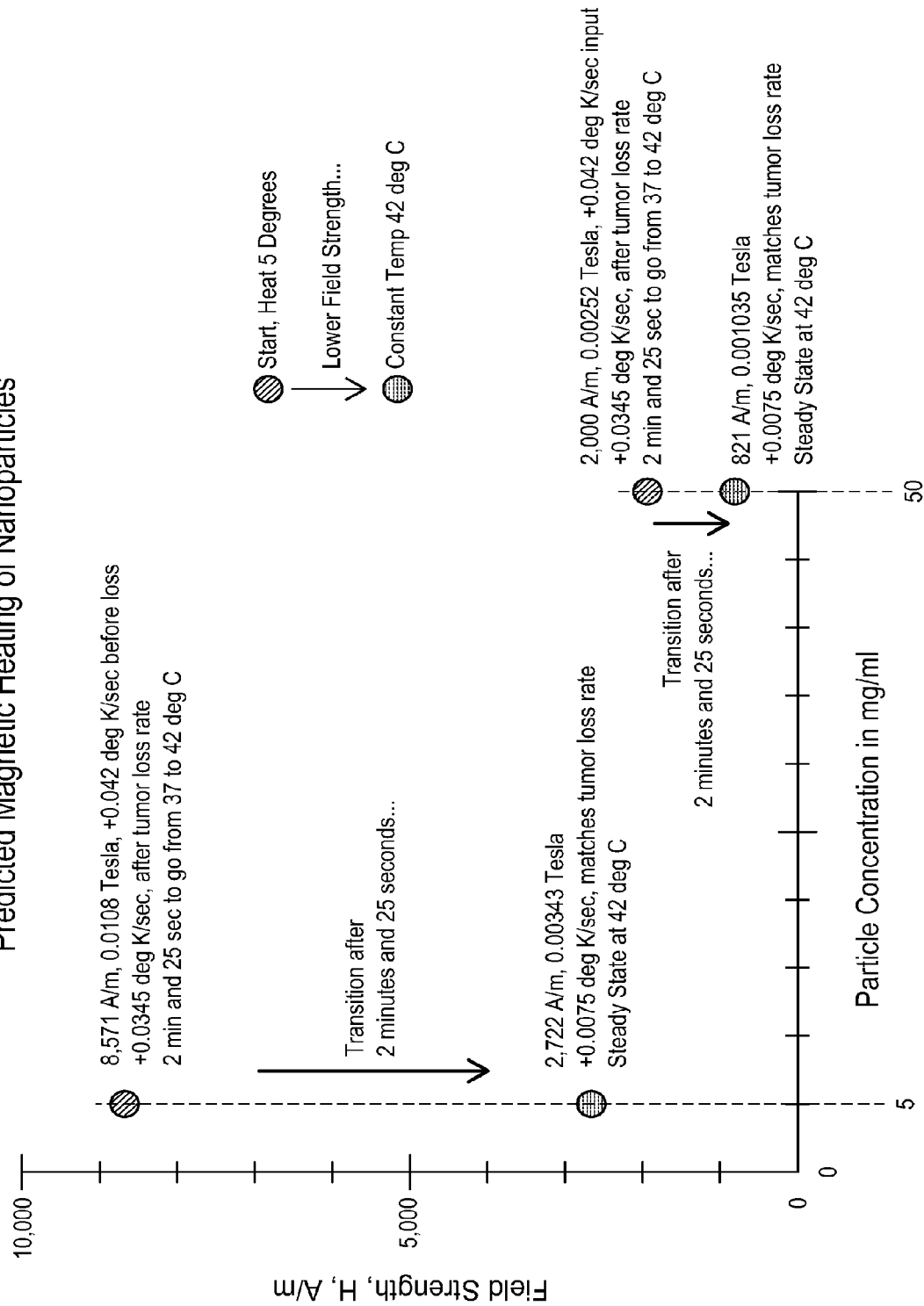
FIG. 10 illustrates in graphical form a plot of the predicted magnetic heating of nano-particles, plotted as a function of field strength vs. particle concentration.

FIGS. 9A and 9B illustrate in graphical form a plot of the experimental resistance of the Helmholtz coil as a function of frequency. FIG. 9A illustrates Litz Wire with 50 strands of 44 AWG wire and FIG. 9B illustrates Litz Wire with 130 strands of 48 AWG wire. The total measured resistance factor is denoted by "X" on the graphs, while the measured skin effect of a straight piece of Litz Wire is marked by "+" on the graphs, and the difference, which is equal to the proximity-effect losses, is marked with "O" on the graphs. Note that for both plots at 50 KHz there is virtually no difference between the DC loss and the AC loss. Thus, this shows conclusively that this problem can be managed by the proper selection of Litz Wire specifications. In practice, measurements show that the relationship to the DC stated resistance (after wound on a coil and measured at the AC frequency of 50 KHz) when using the proper Litz Wire, is no worse than a 4 times multiplier, significantly better than when using a single strand wire.

The Approach

From a systems perspective, there are a number of technical issues that are inherent with the design of the body cavity cancer treatment apparatus. First, the frequency of illumination cannot be too low, otherwise the body's nervous system can be excited; this is known to be in the 2,000 to 3,000 Hz range but practically is below 10,000 Hz. As a measure of safety, the present body cavity cancer treatment apparatus does not generate a magnetic field of frequency below 40 KHz. Next, the nano-particles being excited express predominantly Brownian heating, for this frequency. Brownian heating has the advantage of being able to put the nano-particles into physical motion, in a rotational or partial rotational sense when an AC (Alternating Current) is used to excite the nano-particles. Alternatively, Neel heating occurs when the magnetic domains rotate and the physical nano-particle remains motionless. At around 254 KHz, the magnetic state of the nano-particle is half Brownian and half Neel. Below 254 KHz, Brownian heating begins to dominate; above 254 KHz Neel heating begins to dominate. The nano-particle size (radius) is highly correlated to the realm of heating. Neel uses much smaller nano-particles while Brownian uses larger nano-particles, in a relative sense. Thus, from a physical perspective, at 40 KHz, the optimal nano-particle size is in the 20 nm range. The optimal nano-particle size, from a biological perspective, is in the 15 to 30 nm diameter range. Smaller nano-particles, say in the 7 nm size range, tend to be "trapped" in healthy tissue. Larger nano-particles, say greater than 100 nm, tend to be "attacked" by white blood cells and quickly removed from the body. For a system that uses the nano-particles in a fluid contained in say a cavity or the bladder as an example, this is less of an issue biologically, but the sizing is important from a heating perspective (Brownian heating).

In addition, there are advantages to having the nano-particles in rotational motion to enhance diffusion. For an IV-based nano-particle delivery, having the nano-particles in motion likely enhances the diffusion through the leaky vasculature of a tumor. For bladder cancer, having the nano-particles in motion ensures that uniform heating occurs. Coincidentally, a nano-particle having a diameter of 20 nm is also the optimal size for Brownian heating (which are frequencies below 254 KHz).

To optimize heating for a given value of f*H, lower frequencies are optimal. In this case, the frequencies being considered are 40-75,000 Hz. A researcher by the name of Brezovich learned empirically that if the product of f*H is on the order of $4.85 \times 10^8$, the subject will begin to feel warm, not uncomfortable after one hour of being illuminated at that level. This nominal value of $4.85 \times 10^8$ is termed herein as "One Brezovich Limit".

This heating is due to an Ephi component generated by the magnetic field, which causes eddy currents in the tissue. Since tissue has a real conductivity value, the tissue heats as a result of the eddy currents. To be ultra conservative and have the PH product no greater than one Brezovich limit, the system design does not inadvertently heat healthy tissue from eddy currents.

Assumptions

| | |
|---|---|
| Start Concentration: | 100 mg/ml of $Fe_3O_4$ |
| Start Volume: | 20 ml, of $Fe_3O_4$ |
| Mitomycin-C: | 40 ml (at desired concentration) |
| Add MMC time is: | after 15 pre-heat timeframe |
| Pre-Heat time: | 15 minutes |
| Treatment time: | 60 minutes |
| Cool-down time: | 15 minutes |
| Frequency | 50,000 Hz |
| Field Strength: | varies from 2,000 to 5,000 A/m |
| Particle Composition: | magnetite 1, $Fe_3O_4$ |
| Particle Size: | 18 nm plus 2 nm coating, hydrodynamic volume at 22 nm |
| Viscosity: | assumed bladder fluids approximates water |
| Bladder Start Volume: | 0 ml |
| Bladder Fill Rate: | 40 ml per hour from kidneys |
| Max Bladder Capacity: | 300 ml (can be upwards of 350 ml) |
| Urge to Urinate Point: | 25% of capacity or 75 ml |
| Heat loss rate of Bladder: | 0.02 deg per sec, nominal |

The nominal bladder heat loss rate, per study, is 0.01 to 0.02 deg per second and the max heat loss rate is 0.05 deg per second (muscle is −0.03 deg/sec; kidney is −0.365 deg/sec; spleen is −0.131 deg/sec; liver is −0.124 deg/sec).

Particle Concentration and Heating Rate for a Cavity, Such as the Bladder

The bladder heating protocol described above with respect to FIG. 1B uses magnetite nano-particles with a typical starting concentration of 100 mg/ml. Then, during the treatment protocol, the kidneys further dilute the concentration of the nano-particles together with the bladder removing heat, meaning during the treatment protocol the magnetic field needs to be progressively increased by the body cavity cancer treatment apparatus to keep the nominal treatment temperature at 42° C.

Protocol:
(1) The protocol involves inserting 20 ml of nano-particle magnetite having a concentration of 100 mg/ml; this is 2,000 mg of iron.
(2) Add $Fe_3O_4$ Magnetite solution to bladder via Foley catheter.
(3) Pre-heat bladder for 15 minutes with 1.8° C. of rise every 5 minutes.
(4) Bladder and nano-particle solution in bladder is now nominally at 42° C.-43° C.
(5) Pre-heat Mitomycin-C to 42° C. prior to adding to bladder via Foley catheter.
(6) Then add 40 ml of Mitomycin-C at its stated concentration.
(7) Maintain stasis temp of 5° C. above body ambient for 60 minutes; this is nominally 42° C.-43° C.
(8) During entire procedure, kidneys fill bladder at rate of 40 ml per hour for patients who have been on a no fluids diet (20-40 ml per hour for patients with a no fluids diet).
(9) Cool down to body ambient at 37° C.; this is after one hour with Mitomycin-C on board with applied heat.
(10) Cool down over 15 minutes versus hard shut down from 42° C.-43° C. to 37° C.
(11) Retain Mitomycin-C on board until at least 2 hours of chemotherapy treatment have evolved; one hour with heat applied, the second hour without heat.

Figure 11:
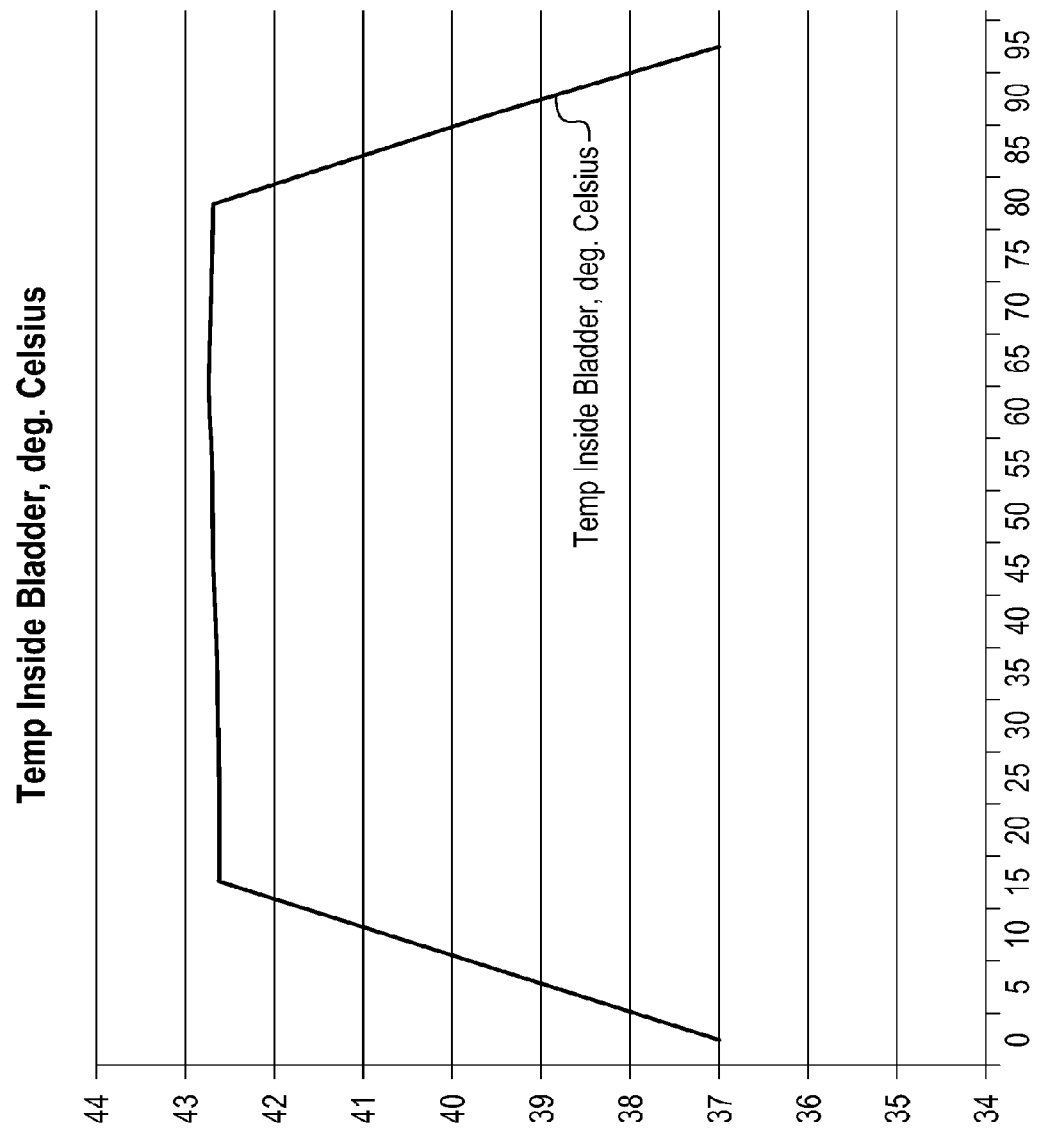
FIG. 11 illustrates in graphical form a plot of the measurement of the typical temperature inside the bladder in degrees Celsius vs. time during the treatment protocol.

Data:

FIGS. 11-15 show the estimated performance of the body cavity cancer treatment apparatus as the particle concentration is diluted and the field rate is adjusted to maintain a stasis temperature of about 5° C. rise above body ambient temperature. FIG. 11 illustrates in graphical form a plot of the measurement of the typical temperature inside the bladder, in degrees Celsius, vs time during the treatment protocol. Pre-heat the bladder for 15 minutes at the determined rise rate of 1.8° C. per every 5 minutes. Reach stasis temperature of 42.5° C. at 15 minutes. At 15 minutes into the procedure, the bladder is at 42° C.-43° C. as shown here. The Y or vertical axis is degrees Celsius and the X or horizontal axis is minutes elapsed. At 15 minutes into the procedure, 40 ml of Mitomycin-C is added (which is pre-heated to 42° C.); to maintain temperature, the field strength is increased to 2,500 A/m. The particle concentration is further diluted by the kidneys producing urine at 40 ml per hour. Therefore, the field strength must be increased at the given rate, moving from 2,500 A/m to just over 3,000 A/m. The maximum field strength is a little greater than 3,000 A/m. This is 0.3 times the nominal one Brezovich limit to avoid eddy currents inadvertently heating the tissue. The Brezovich limit is the frequency times the field strength divided by a constant of 4.85E8. Only the particles heat via magnetic Brownian excitation, and then via fluid convection, the bladder tissue heats; no other tissue inadvertently heats, such as occurs with existing prior art treatment methods.

In Brownian excitation, the nano-particles actually physically rotate, based on the frequency of illumination and the viscosity of the fluid containing the particles. For this particular particle size, frequency and fluid viscosity, there is a very small contribution from Neel heating, but since it is de minimus, it is not considered. Neel heating is when the magnetic domains align and un-align; this process causes heat. In Neel heating, the particles do not physically move.

Figure 12:
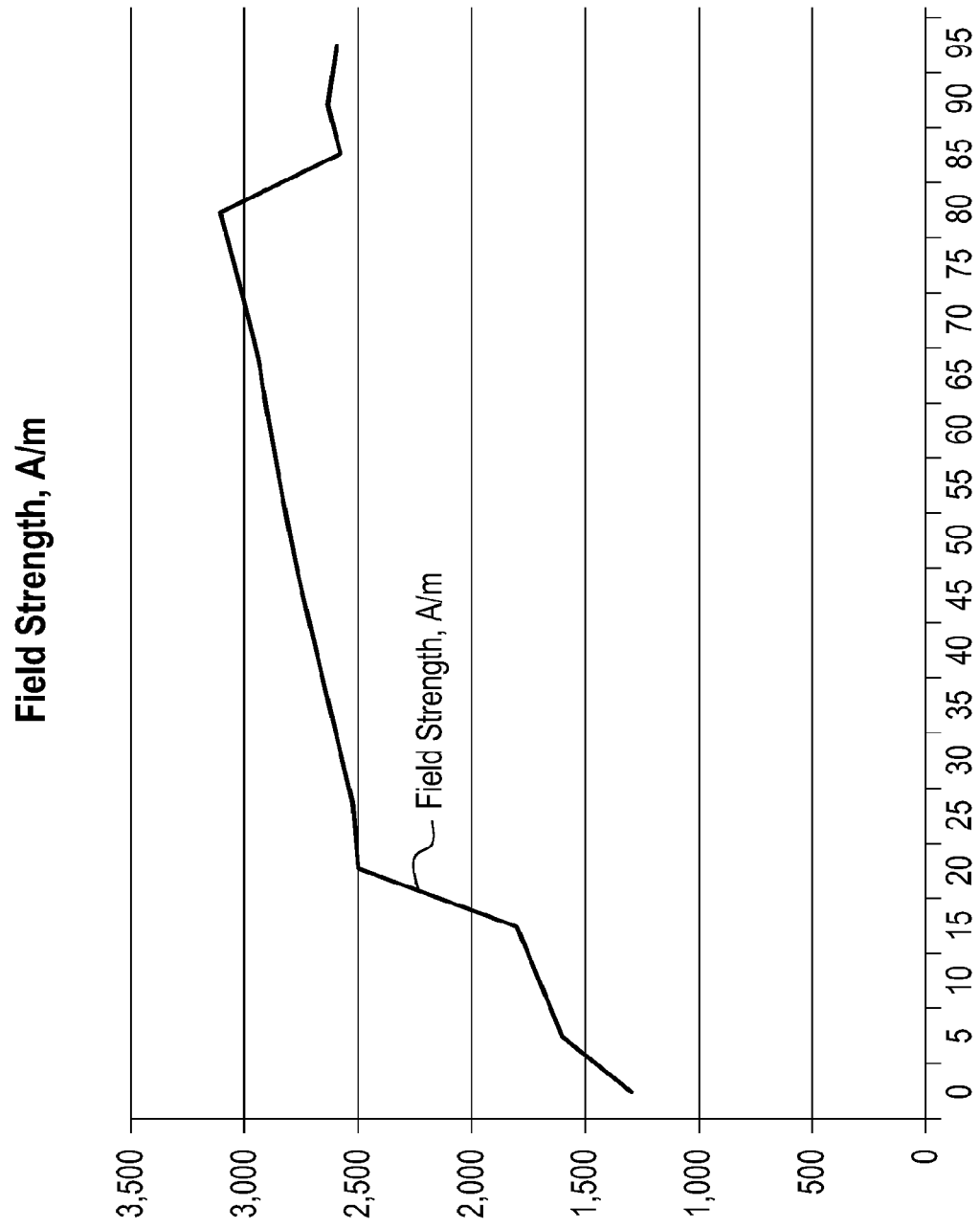
FIG. 12 illustrates in graphical form a plot of the measurement of the typical field strength in Amps/meter vs. time during the treatment protocol.
Figure 13:
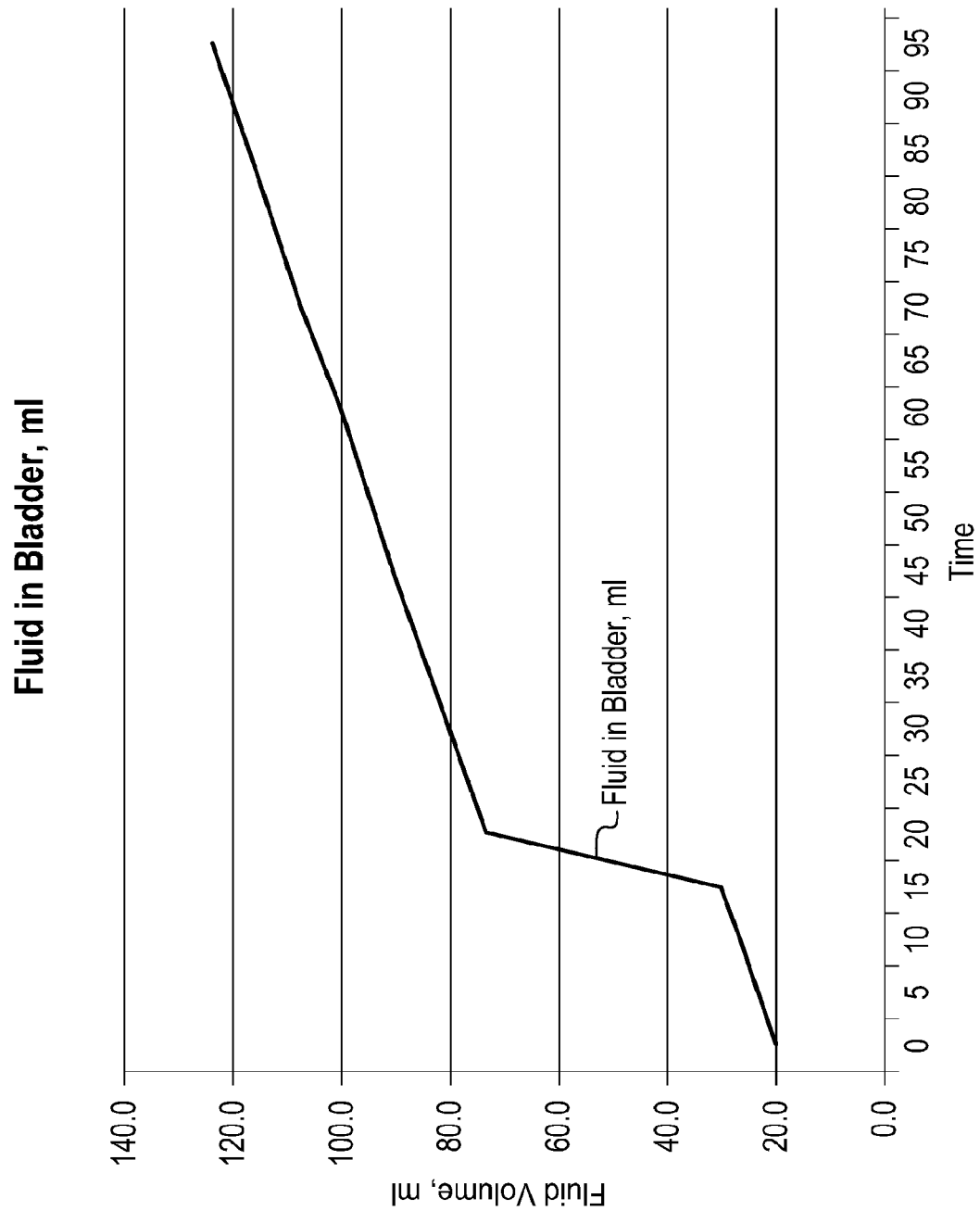
FIG. 13 illustrates in graphical form a plot of the measurement of the typical bladder fluid volume in milliliters vs. time during the treatment protocol.

FIG. 12 illustrates in graphical form a plot of the measurement of the typical field strength in Amps/meter vs. time during the treatment protocol (vertical or Y axis) with the horizontal or X axis as time in minutes. FIG. 13 illustrates in graphical form a measurement of the typical bladder fluid volume in milliliters during the treatment protocol. Initially, 20 ml of Mitomycin-C are added, which is the 100 mg/ml concentration of $Fe_3O_4$. At 15 minutes into the procedure, 40 ml of Mitomycin-C are added. Throughout the process, from time=zero, the kidneys are adding 40 ml per hour of urine. At 25% of full bladder volume of say 300 ml (or 75 ml]), the patient begins to feel an urge to vacate the bladder. At 120 m of volume, the urge to void the bladder has grown a bit but should be "patient tolerable" based on studies and research. FIG. 13 illustrates in graphical form a plot of the measurement of the typical bladder fluid volume in milliliters vs. time during the treatment protocol; the Y axis is in milliliters and the X axis is in minutes of time. The particle concentration falls to below 20 mg/ml near the end of the treatment cycle. That is because the procedure started with a particle concentration of 100 mg/ml and then because of dilution from the added Mitomycin-C and the contribution from the kidneys, the end resulting nano-particle concentration is just below 20 mg per milliliter.

Figure 8:
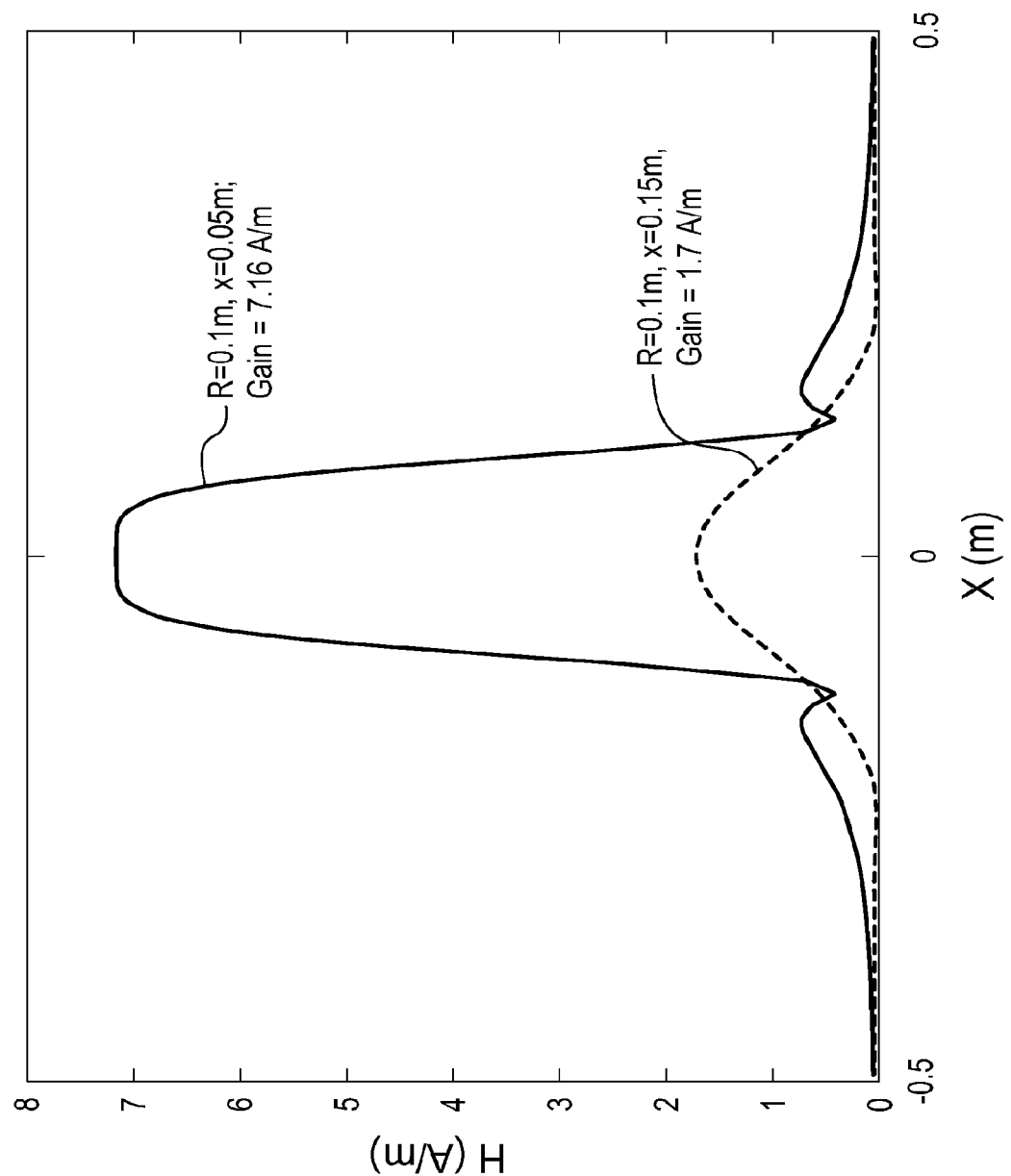
FIG. 8 illustrates in graphical form, a plot of the overall "gain" of a Helmholtz coil system, as generated by a computer modeling system.

Since the system is not near the design maximum of 10,000 A/m, there is sufficient field strength availability to heat even lower concentrations. FIG. 8 illustrates in graphical form a plot of the theoretical overall gain of a Helmholtz coil system, as generated by a computer modeling system. The minimum concentration shown in mg/ml is on the order of 5 mg/ml; any concentrations below that level are difficult to heat. The 5 mg/ml fields were 8,571 A/m, which is believed to be too high to keep eddy currents to the proper level to minimize healthy tissue heating, so a higher concentration is preferable. Other procedures that add greater amounts of fluid might need to start with higher nano-particle concentrations. It is believed that for magnetite $Fe_3O_4$ in a water-based solution, the maximum concentration is in the 250-300 mg/ml range before it begins to become too thick and viscous to be practical to use.

Figure 14:
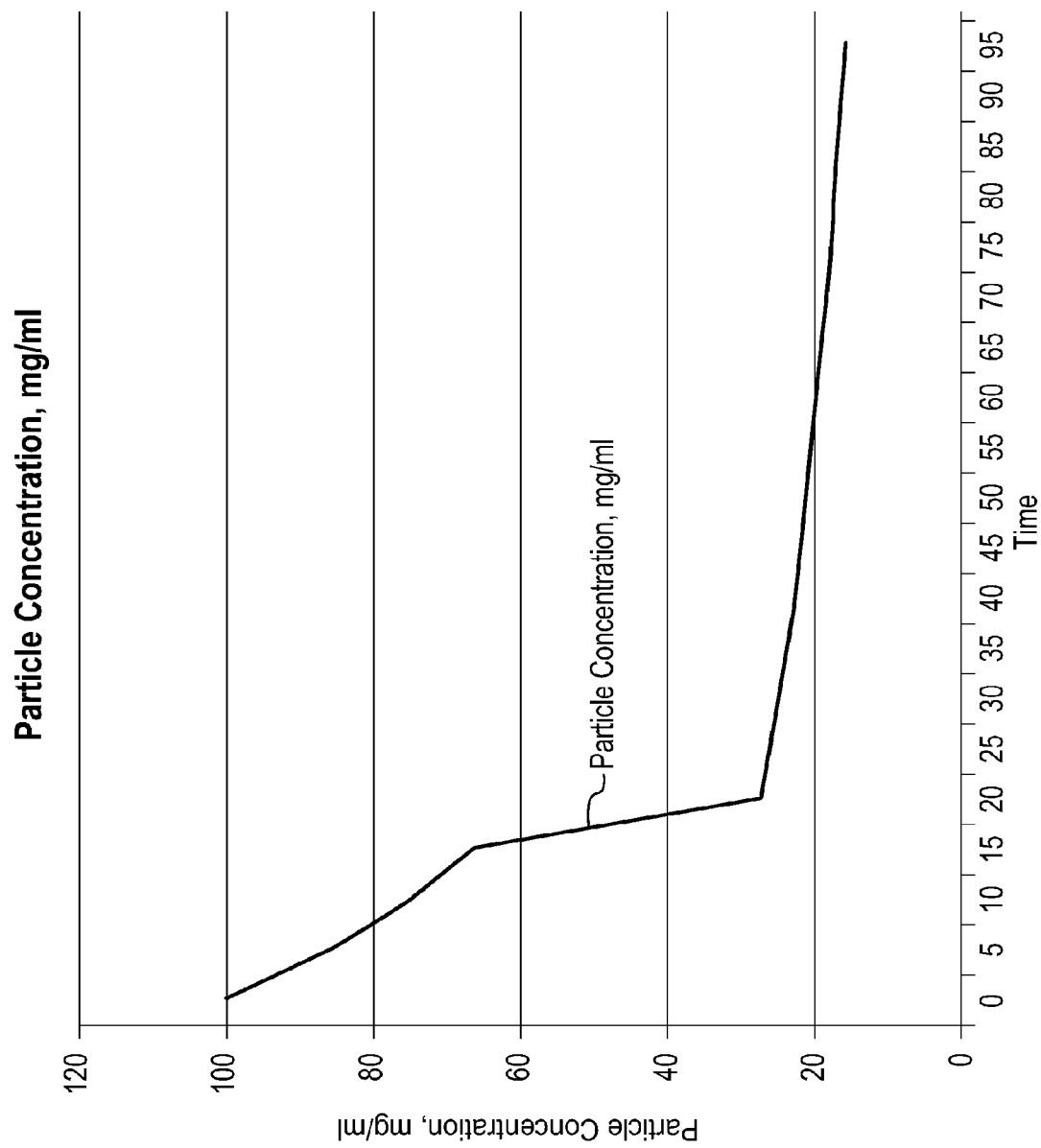
FIG. 14 illustrates in graphical form a plot of the measurement of the typical particle concentration in milligrams/milliliter vs. time during the treatment protocol.
Figure 15:
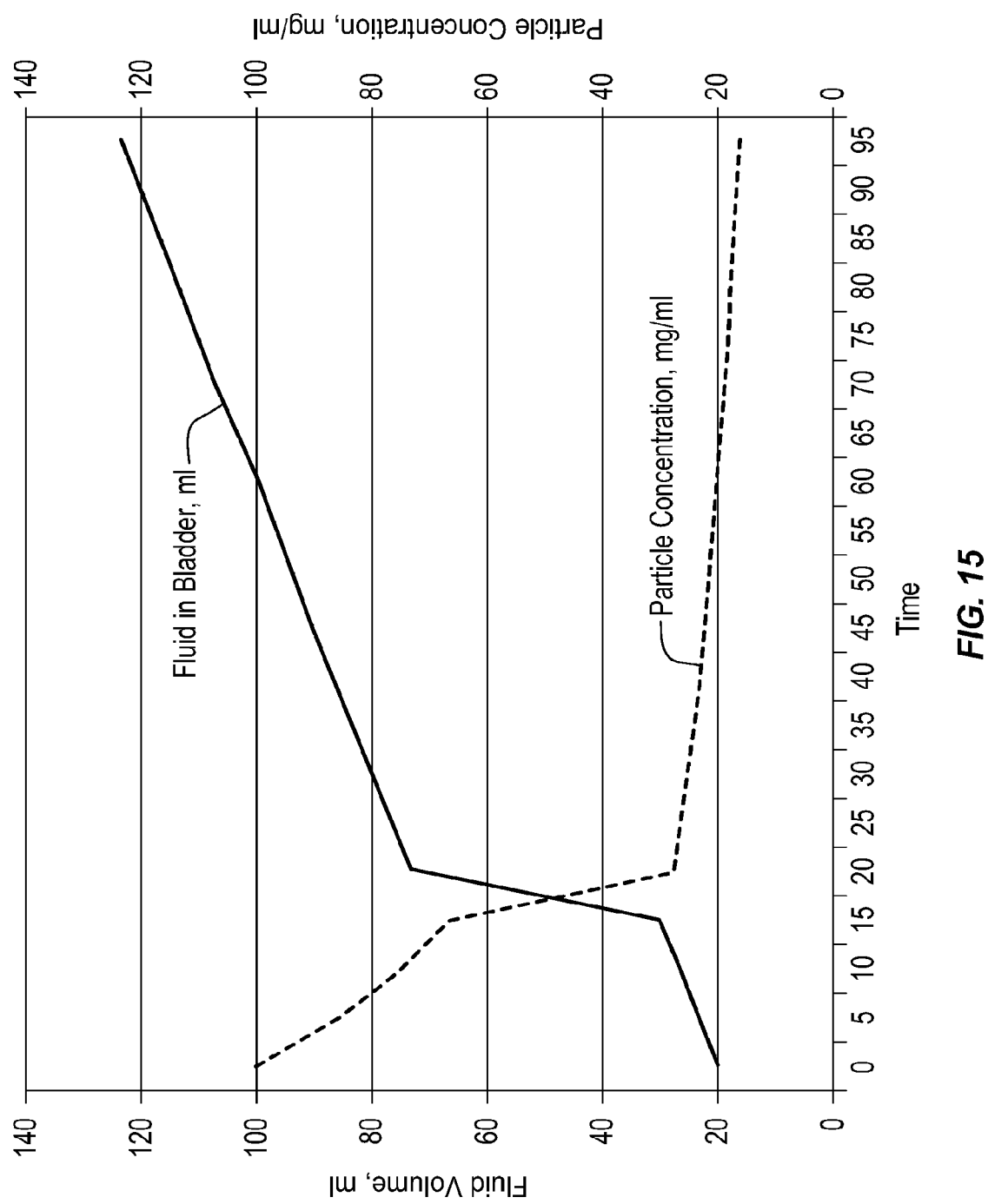
FIG. 15 illustrates in graphical form a plot of the measurement of the typical particle concentration in milligrams/milliliter during the treatment protocol as overlaid on the typical bladder fluid volume in milliliters vs. time during the treatment protocol.
Figure 16:
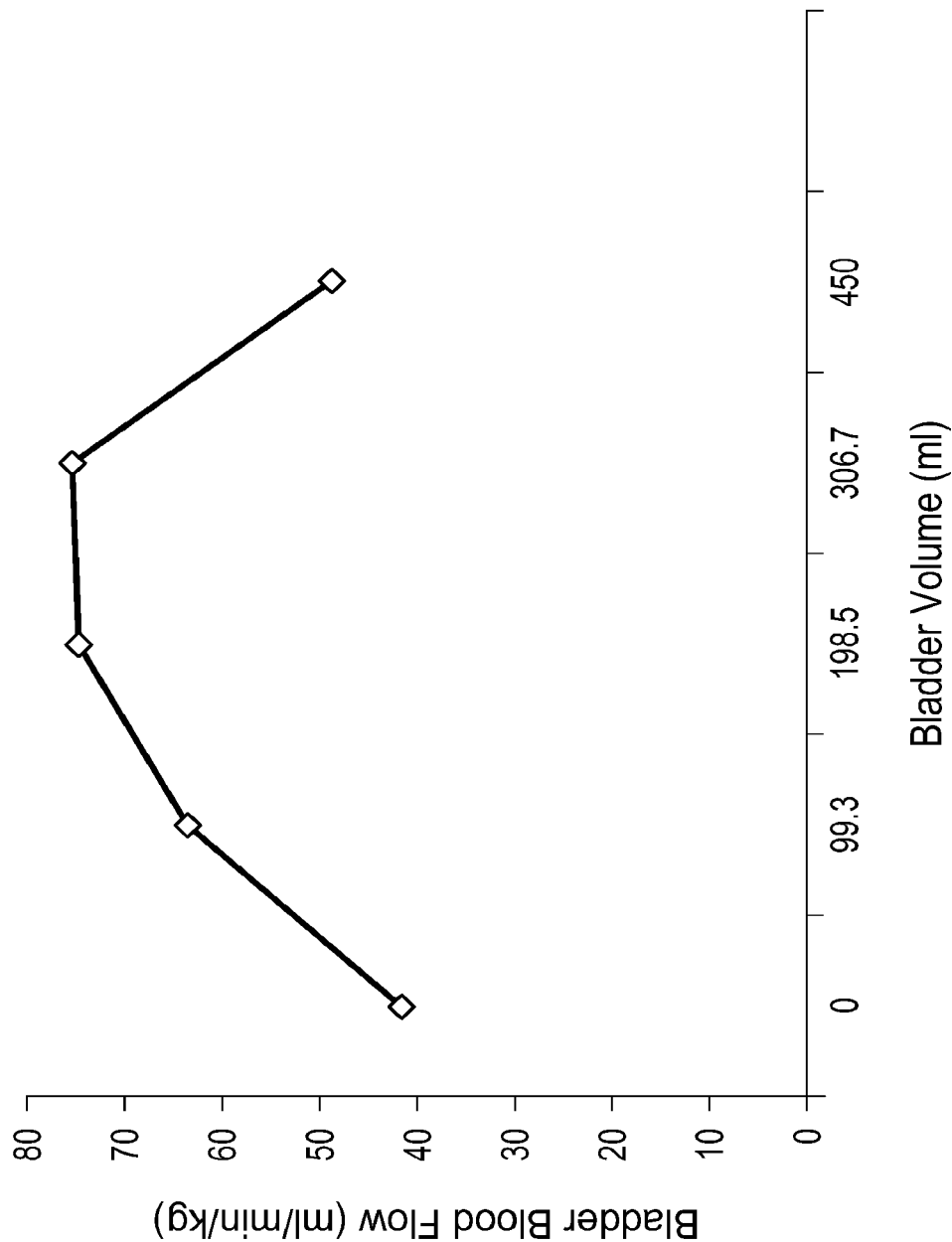
FIG. 16 illustrates in graphical form a plot of bladder blood flow vs bladder volume.

FIG. 14 illustrates in graphical form a plot of the measurement of the typical particle concentration in milligrams/milliliter vs. time during the treatment protocol. It starts at 100 mg/ml, and then thru various dilutive steps, it ends up in the 19 mg/ml range. At 15 minutes in, the Mitomycin-C is added (40 ml) and then kidney-based dilution at a flow rate of a patient who has been on a no-liquids diet. FIG. 15 illustrates in graphical form a plot of the measurement of the typical particle concentration in milligrams/milliliter vs. time during the treatment protocol as overlaid on a plot of the typical bladder fluid volume in milliliters vs. time during the treatment protocol.

The Actium Condition

The Actium Condition is a state where nano-particle heating is optimized while the probability of tissue heating via unintended eddy currents is minimized. Brezovich, when he created the condition of PH with respect to a constant of 4.85E8, did not do so in the context of nano-particle heating. He was only concerned with the unintended creation of eddy currents which heats tissue not having nano-particles, which in reality is measured to be f*H2. When the context of nano-particle heating is added to a fixed value of f*H2, an optimal operating point with respect to frequency is realized. Since the particle heating, prior to particle magnetic saturation, is a function of the field strength squared, it is desirable to maximize the field strength versus frequency. This means lower frequencies with a given field strength yield significantly higher rates of nano-particle heating without creating unintended eddy currents which heat tissue, not nano-particles.

Since the frequency needs to be at least above 10 KHz to avoid nerve/muscle excitation, a safety zone is created by heating the nano-particles at 40 KHz, well above the frequencies where nerves are excited. Since PH is the second constraint, the field strength for one Brezovich limit (an Actium-derived term) is 9,700 A/m. Since this study shows a maximum field strength of around 3,100 A/m, the body cavity cancer treatment system now operates a level of 0.3 Brezovich limits—thus, the heating of the particles is optimized while the possibility of unintended eddy currents is minimized.

The Helmholtz Coil Magnetic Fields

The Helmholtz Coil configuration is:
Coil Spacing is 30 cm
Coil Diameter is 60 cm
420 turns per coil
10 cm of wound wire thickness
Around 207 pounds of copper weight alone
21 turns in Z and 20 turns in X-Y
Spacing between wires is 5.08 mm; about 0.2 inches
Current on each coil (each wire) is 10 amps The uniform field volume is 11.8 inches in height by 13.8 inches in body width by 13.8 inches in body length which is equivalent to 2,246 cubic inches.

As previously discussed, when the wire thickness progresses from an infinitely thin wire to 4 inches of hundreds of wires, there is a 16% loss of field strength from the theoretical predicted value using the Helmholtz equation. When this coil is built in practice, sub-coils in the Z-direction will be used to obtain resistances, voltages and currents that are within the specifications of the selected components of the machine. These sub-coils would be a minimum of 4 divisions of the 420 windings, as previously discussed.

At 50 KHz frequency, the four field strengths for the four Brezovich limits are:

| One Brezovich Limit | 9,700 A/m |
| Two Brezovich Limits | 19,400 A/m |
| Three Brezovich Limits | 29,100 A/m |
| Four Brezovich Limits | 38,800 A/m |

| Field Strengths | 50 mg/ml |
| Heating to 42 deg C. | 2,000 A/m |
| Steady State | 821 A/m |

This corresponds to the following Brezovich limits; note that only during heating to 42° C. at the lowest concentration do we even approach one Brezovich limit. The rest of the time, particularly the steady state heating timeframe, the Brezovich limit levels are very low. We are at 0.88 Brezovich limit at our maximum operating level when heating a 5 mg/ml particle concentration for 2 minutes and 25 seconds to 42° C. All other points in our heating protocol are at significantly lower levels.

| Brezovich Limits, 50KHz | 50 mg/ml |
| Heating to 42 deg C. | 0.21 Brezovich Limits |
| Steady State | 0.08 Brezovich Limits |

At one Brezovich limit, virtually zero unintended tissue heating occurs, even in muscle. The previous table shows that in normal operation, we are typically in the 0.3 Brezovich limit level and lower. This means it is virtually impossible for us to heat tissue in a magnetic field (without particles), much less exceed the SAR maximums stated for MRIs.

The Bladder Heating Model with Eddy Currents

Separately, full body models have been completed using a second simulation step where biological heat removal models such as the Pennes Bio Heat Equations predict what the body's heating is from the eddy currents. The Thermal model yielded a complete body temperature analysis which showed that for the 2,500-3,000 A/m illumination protocol previously shown, for the bladder example, the average tissue temperature from eddy currents is in the neighborhood of 0.4° Celsius . . . virtually indistinguishable. The peak temperature from eddy currents was seen to be around 0.9° C. for a very small tissue region. In addition to keeping the f*H product low, and keeping the magnetic field strength low (H), there are many other methods in the toolbox to manage eddy currents and unintended tissue heating.

It is important to note that the methods discussed next, to lower the probability and level of unintended tissue heating, are not necessary or required since the examples provided herein heat just fine. They are merely ideas and concepts created to use should this ever become an issue. Methods to manage unintended tissue heating:

1. Use Mu Metal to shield certain areas of the body.
2. Use active magnetic field cancellation (discussed next).
3. Use higher magnetic nano-particle concentrations—the bladder example used 100 mg/ml of 20 nm sized $Fe_3O_4$. It is believed that starting nano-particle fluid concentrations can go upwards of 300 mg/ml; this means that the field strength needed, hence reduced eddy current levels, and is improved.
4. Use the lowest fluid levels possible for both the nano-particles as well as the applied chemotherapy agent. Lower dilution means higher heating with lower magnetic field strengths.
5. Lower the excitation frequency slightly to 30-40 KHz. A lower frequency means a higher field strength can be used, which yields faster nano-particle heating in contrast to any created eddy currents.
6. Optimize the nano-particle size distribution to only have nano-particles which are at the desired size of nominally 20 nanometers in diameter (hydrodynamic size).
7. Increase the magnetization of the nano-particles. By increasing the magnetization of the nano-particles, the nano-particles heat at a significantly greater rate for a given applied magnetic field.
8. Apply a DC magnetic field in the areas where zero AC magnetic field is needed; a DC magnetic field tends to counter or reduce the magnitude of the AC magnetic field.
9. Use a grounding strip on the body to short out any surface currents on the body.
10. Change the position of the Helmholtz coils (other) to a position which minimizes the formation of eddy currents.
11. Use a carbon-loaded blanket on the body parts not being illuminated with the magnetic field. Eddy currents can exist beyond the area where the B, H field exists, and so these areas would be "absorbed".

Blocking or Shielding Vital Organs

When the nano-particles are delivered via an IV or intravenous tubes, the nano-particles that are not taken up by the cancer are eventually removed by the body's filtering organs. This is not an issue for the "cavity" method such as for the bladder. Certain vital organs which are responsible for filtering out foreign objects from the body include the kidneys, the spleen and the liver. These vital organs remove nano-particles from the body which are not taken up in a cancerous region. It is conceivably possible that these organs could have nano-particles residing in them during a magnetic illumination protocol for cancer, where nanoparticles purposefully reside in the cancerous region. It is desirous to block or shield these vital organs from illumination of the magnetic field to a level at least one order of magnitude, as an initial design objective. One order of magnitude in field reduction typically yields a 50 times reduction in heating rate (for the assumptions listed below).

Given that heating is a function of the magnetic field squared, a ten times reduction of the magnetic field results in a heating rate reduction of 50 times (Brownian heating, viscosity is 2× water, 40 KHz, 50 mg/ml, 20 nm diameter particles). The heating rate at 8,600 A/m is 0.4073° K/sec while the heating rate at 860 A/m is 0.0082° K/sec for a heating ratio of around 50 times (again, both are for 20 nm diameter particles). The field strength of 8,600 A/m is only used during the 2-3 minute heating phase from 37° C. to 42° C.

In practice, when at 42° C., the rate of heat input need only match the rate of heat loss to stay at 42° C. The average tumor heat loss rate is 0.0075 deg/sec. However, healthy tissue has an average heat loss rate significantly higher due to the more organized and more efficiently operating blood perfusion in healthy tissue. In a person that has cancer, the liver/kidneys/spleen could be taxed and working overtime to try and rid the body of cancerous cells, but the vital organs should have better perfusion and should be able to remove heat at a much higher rate than cancer.

During the steady state phases of maintaining a continuous temperature of 42° C., the field strength at 50 mg/ml is 2,722 A/m. Our target field strength for the vital organs is 272 A/m or less (one tenth or less the incident field strength in the cancerous region). At 272 A/m, the field strength is 0.0003427 Tesla (for the spreadsheet input); the particle concentration is assumed to be 50 mg/ml in the vital organs. Putting this Tesla value into computer models for Brownian heating, we get plus 0.0008° K/sec heat added into the vital organ containing nano-particles at 50 mg/ml.

Even fat, with its very poor blood perfusion, has a heat loss rate of minus 0.003 deg/sec; this means that even fat would easily remove this very low added heat with zero net temperature increase. The vital organs, with their enhanced perfusion, even if impaired in a cancer patient, would easily remove this level of added heat (plus 0.0008° K/sec). Thus, a ten times reduction in field strength for the vital organs seems to be a good starting point for the design goal of our blocking or shielding algorithms.

The heat loss rates for healthy vital organs is decidedly greater than that for other tissue types due to the large supply of blood perfusion. The kidney is negative 0.365 deg per second, the liver is negative 0.124 deg per second and the spleen is negative 0.131 deg per second. These heat loss rates swamp the plus 0.0008 deg/sec heating rate after a ten times reduction in field strength is applied (50 mg/ml, 272 A/m or lower).

Thus, a ten times reduction in field strength in the volumetric region of vital organs is sufficient (ten times lower than the treatment field strength in the cancerous volumetric region). The natural heat loss rates of these organs further ensures that these organs, when they are removing nano-particles, in concert with a low-level applied field, will not heat at all.

It is possible that 42° C. is not optimal, or is not optimal for a given person with a given cancer. Nothing herein limits these concepts to a fixed temperature of 42° C. The system can be adjusted to realize any new temperature, say 44° C. For example, some studies have indicated that 15 minutes at 44° C. is equivalent to 1 hour at 42° C. in terms of its biological benefit and effect.

At less than one Brezovich limit, the body cavity cancer treatment apparatus causes virtually no unintended heating via eddy currents in tissue without particles. When compared to MRI maximum SAR limits (Specific Absorption Ratio), the Actium system is many orders of magnitude below the stated MM heating maximums (MRI's use magnetic fields at higher frequencies). When running a full body model for a bladder cancer heating example at 3,000 A/m, the average temperature caused by an eddy current is plus 0.4° C. over body ambient—virtually zero. The fluid in the bladder is heated to a nominal 42° C. for a full hour or longer by using a magnetite nano-particle fluid in the bladder susceptible to heating by a magnetic field. It is important to protect organs that may have filtered out nano-particles if the nano-particles are delivered via IV. Organs that may have taken up nano-particles include the spleen, liver and kidneys. The first method is passive and uses a material that has a very high relative magnetic permeability (Ur of 80,000 to 100,000) to block the fields. This material would be used above and below the body in the region of the vital organs. The second method is active and involves the use of a smaller excited coil inside the larger 60 cm coil. By varying or adjusting both the magnitude and phase of the drive current of the smaller blocking coil, the fields can be cancelled in the region of the vital organs. Note that for either method, passive vs. active, energy is not destroyed, meaning the magnetic fields are not destroyed; rather, the fields are re-directed or re-shaped away from the vital organs when the nano-particles are delivered via IV.

Field strengths sufficient to heat nano-particles at very low concentrations are easily achieved. The product of the excitation frequency and the field strength is sufficiently low to not cause unintended tissue heating while at the same time optimizing the heating of nano-particles in the Brownian magnetic region. Finally, the body's filtering organs, containing nano-particles, can be shielded so that they do not heat during a cancer treatment protocol. The tools available in the toolbox are versatile and many, there is nothing that cannot be solved.

The concept of using the body's natural cavities, or the creation of temporary cavities, enables very precise control of the nano-particles and the illumination process is very easily implemented. In addition, after the heating protocol is completed, the nano-particles are completely or nearly completely removed. This eliminates much of the issues and operating concerns if the nano-particles are delivered via IV.

SUMMARY

The body cavity cancer treatment apparatus generates the magnetic field for use in a combined "low temperature hyperthermia" and ionizing radiation and/or chemotherapy cancer treatment protocol. Unlike other competing systems, the body cavity cancer treatment apparatus does not directly kill or ablate the cancer cells with killing temperatures; rather, the body cavity cancer treatment apparatus stresses the cancer and cancer stem cells by keeping them at a nominal 42° C. for some period of time via the heating of nano-particles that have been infused into the bladder, using the generated magnetic field.

What is claimed as new and desired to be protected by Letters Patent of the United States is:

1. A system for treating cancer located in a cavity in an organ within a body, the cavity having a tissue surface and a cavity temperature, the system comprising:
    a solution of iron oxide nanoparticles introduced directly into the cavity, the solution in contact with the tissue surface of the cavity;
    a chemotherapy agent introduced directly into the cavity;
    a table for positioning the body containing the cavity;
    two coreless coils positioned for generating a treatment AC magnetic field that extends through the cavity of the body located on the table;
    at least two temperature measurement probes for sensing a temperature of the solution in the cavity to generate a sensed solution temperature;
    a control computer in communication with an Automatic Frequency Control (AFC) circuit, the control computer configured for applying a drive current to the coreless coil to generate the treatment AC magnetic field and for regulating the drive current to the coreless coil to raise the cavity temperature at a predetermined rate and to maintain the cavity at a predetermined temperature for a predetermined time in response to the sensed temperature of the solution in the cavity;
    wherein the magnetic field has a frequency between 30 kHz and 100 kHz; and
    wherein the cavity is disposed in an organ selected from the group comprising a bladder, a breast, a cervix, a colon, a uterus, a vagina, an esophagus, a stomach and a brain; the cavity either being naturally occurring or created therein.

2. The system of claim 1 wherein the solution of iron oxide nanoparticles has a concentration between 20 mg/ml and 300 mg/ml.

3. The system of claim 1 wherein the predetermined rate of rise of temperature of the cavity is 0.0008° K/sec to 0.407° K/sec.

4. The system of claim 1 wherein the predetermined time is between 15 and 60 min.

5. The system of claim 1 further comprising a catheter for introducing the solution of iron oxide nanoparticles into the cavity for treatment and for removing the solution of iron oxide nanoparticles from the cavity after treatment.

6. The system of claim 1 wherein the predetermined temperature is between 42° C. and 43° C.

7. The system of claim 1 further comprising a catheter for introducing the solution of nanoparticles into the cavity for treatment and removing at least a portion of the solution of nanoparticles from the cavity after treatment.

8. The system of claim 1 further comprising a shield to protect portions of the body that need to be shielded from the treatment AC magnetic field.

9. The system of claim 1 wherein the two coreless coils comprise a Helmholtz configuration.

10. A method for treating cancer located in a cavity in an organ within a body, the cavity having a tissue surface and a cavity temperature, the method comprising the steps of:
    introducing a solution of iron oxide nanoparticles directly into the cavity, the solution in contact with the tissue surface of the cavity;
    introducing a chemotherapy agent directly into the cavity;
    positioning the body containing the cavity on a table;
    positioning two coreless coils for generating a treatment AC magnetic field that extends through the cavity;
    sensing a temperature of the solution in the cavity using at least two temperature measurement probes to generate a sensed solution temperature;
    applying, using a control computer in communication with an Automatic Frequency Control (AFC) circuit, a drive current to the coreless coil to generate the treatment AC magnetic field and regulating the drive current to the coreless coil using the control computer to raise the temperature of the cavity at a predetermined rate and to maintain the cavity at a predetermined temperature for a predetermined time in response to the sensed solution temperature in the cavity;
    wherein the treatment AC magnetic field has a frequency between 40 kHz and 75 kHz; and
    wherein the cavity is disposed in an organ selected from the group comprising a bladder, a breast, a cervix, a colon, a uterus, a vagina, an esophagus, a stomach and a brain; the cavity either being naturally occurring or created therein.

11. The method of claim 10 wherein the solution of iron oxide nanoparticles has a concentration between 20 mg/ml and 300 mg/ml.

12. The method of claim 10 wherein the predetermined rate of rise of temperature of the cavity is 0.0008° K/sec to 0.407° K/sec.

13. The method of claim 10 wherein the predetermined time is between 15 and 60 min.

14. The method of claim 10 further comprising the step of removing the iron oxide nanoparticles from the cavity after treatment.

15. The system of claim 10 wherein the predetermined temperature is between 42° C. and 43° C.

16. The method of claim 10 further comprising the step of shielding, with a magnetic field shield, portions of the body that need to be shielded from the treatment AC magnetic field.

17. The method of claim 16 wherein the step of shielding portions of the body that need to be shielded from the treatment AC magnetic field comprises applying a DC magnetic field to the portions of the body to be shielded.

18. The method of claim 16 wherein the step of shielding portions of the body that need to be shielded from the treatment AC magnetic field comprises applying a cancelling AC magnetic field to the portions of the body not to be exposed to the treatment AC magnetic field, the cancelling AC magnetic field having a phase different from the phase of the treatment AC magnetic field.

19. The method of claim 16 wherein the shield is a magnetic permeability material having a relative permeability of greater than $8 \times 10^4$.

20. The method of claim 10 wherein the two coreless coils comprise a Helmholtz configuration.

\* \* \* \* \*